(12) United States Patent
Payeur et al.

(10) Patent No.: US 9,484,702 B2
(45) Date of Patent: Nov. 1, 2016

(54) SYSTEM AND METHOD FOR AGILE REMOTE GENERATION OF A BROADBAND TUNABLE SHORT-PULSE EMISSION

(75) Inventors: Stéphane Payeur, Montreal (CA);
Philippe Lassonde, Montreal (CA);
Jean-Claude Kieffer, Montreal (CA);
Francis Théberge, Shannon (CA);
Marc Châteauneuf,
Saint-Augustin-de-Desmaures (CA);
Jacques Dubois, Quebec (CA)

(73) Assignee: INSTITUT NATIONAL DE LA RECHERCHE SCIENTIFIQUE, Québec (CA)

( * ) Notice: Subject to any disclaimer, the term of this patent is extended or adjusted under 35 U.S.C. 154(b) by 729 days.

(21) Appl. No.: 13/428,397

(22) Filed: Mar. 23, 2012

(65) Prior Publication Data

US 2012/0243564 A1   Sep. 27, 2012

Related U.S. Application Data

(60) Provisional application No. 61/466,580, filed on Mar. 23, 2011.

(51) Int. Cl.
*H01S 3/00* (2006.01)
*G02F 1/35* (2006.01)
*G01N 21/3581* (2014.01)

(52) U.S. Cl.
CPC .......... *H01S 3/0057* (2013.01); *G02F 1/3511* (2013.01); *H01S 3/0078* (2013.01); *G01N 21/3581* (2013.01); *G02F 2001/3528* (2013.01); *H01S 3/0092* (2013.01)

(58) Field of Classification Search
CPC .. H01S 3/0057; H01S 3/0078; H01S 3/0092; G02F 1/3511; G02F 2001/3528
USPC .......................................................... 372/21
See application file for complete search history.

(56) References Cited

U.S. PATENT DOCUMENTS

| | | | | |
|---|---|---|---|---|
| 5,210,764 A * | 5/1993 | Bucher et al. | ................... | 372/23 |
| 5,579,152 A | 11/1996 | Ellingson et al. | | |
| 6,700,905 B1 | 3/2004 | Karasawa et al. | | |
| 7,729,044 B2 * | 6/2010 | Theberge et al. | ............. | 359/330 |
| 2005/0041702 A1 * | 2/2005 | Fermann | ................... | G02F 1/39 372/25 |
| 2005/0169326 A1 * | 8/2005 | Jacob et al. | ..................... | 372/22 |

OTHER PUBLICATIONS

Francis Théberge et al., "Generation of tunable and broadband far-infrared laser pulses during two-color filamentation", Physical Review A 81, 033821 (2010).

(Continued)

*Primary Examiner* — Xinning Niu
(74) *Attorney, Agent, or Firm* — Gwendoline Bruneau

(57) ABSTRACT

A method comprising using a pulse shaper in the spectral domain to generate multiple-color pulses directly at the output of the laser amplifier. The delay can thus be controlled directly in the spectral domain and there is no need for an optical delay line. The method allows reducing the number of optical components and insures insensitivity to alignment, vibrations and turbulence on long distance propagation and filamentation, particularly in air. The method allows programmable and tunable interaction, since the pulse shaper is able to control the laser spectral amplitude and phase.

23 Claims, 26 Drawing Sheets

(56) References Cited

OTHER PUBLICATIONS

Francis Théberge et al., "Tunable ultrashort laser pulses generated through filamentation in gases", Physical Review Letters 97, 023904 (2006).
Francis Théberge et al., "Ultrabroadband conical emission generated from the ultraviolet up to the far-infrared during the optical filamentation in air", Optics Letters, vol. 33, No. 21, Nov. 1, 2008.
Benjamin Clough et al., ""All air-plasma" terahertz spectroscopy", Optics Letters, vol. 36, No. 13, Jul. 1, 2011.
D. J. Cook et al., "Intense terahertz pulses by four-wave rectification in air", Optics Letters, vol. 25, No. 16, Aug. 15, 2000.
Jianming Dai et al., "Coherent polarization control of terahertz waves generated from two-color laser-induced gas plasma", Jul. 10, 2009.
Takao Fuji et al., "Generation of sub-two-cycle mid-infrared pulses by four-wave mixing through filamentation in air", Optics Letters, vol. 32, No. 22, Nov. 15, 2007.
Takao Fuji et al., "Generation of 12 fs deep-ultraviolet pulses by four-wave mixing through filamentation in neon gas", Optics Letters, vol. 32, No. 17, Sep. 1, 2007.
J. Kasparian et al., Infrared extension of the supercontinuum generated by femtosecond terawatt laser pulses propagating in the atmosphere, Optics Letters, vol. 25, No. 18, Sep. 15, 2000.
Thomas Oksenhendler et al., Intravavity acousto-optic programmable gain control for ultra-wide-band regenerative amplifiers, Applied Physics B 83, 491-495 (2006).
Thomas Oksenhendler et al., "Ultrawideband regenerative amplifiers via intracavity acousto-optic programmable gain control", Conference on Lasers and Electro-Optics (CLEO) Long Beach, California, May 21, 2006.
F. Verluise et al., "Amplitude and phase control of ultrashort pulses by use of an acousto-optic programmable dispersive filter: pulse compression and shaping", Optics Letters, vol. 25, No. 8, Apr. 15, 2000.
Y. Zhang et al., "Non-radially polarized THz pulse emitted from femtosecond laser filament in air", Optics Express, vol. 16, No. 20, Sep. 29, 2008.
A. Couairon et al., "Propagation of twin laser pulses in air and concatenation of plasma strings produced by femtosecond infrared filaments", Optics Communications 225, 177-192 (2003).
X. Xie et al., "Coherent control of THz wave generation in ambient air", Physical Review Letters 96, 075005 (2006).
K.Y. Kim et al., "Coherent control of terahertz supercontinuum generation in ultrafast laser-gas interactions", Nature photonics, vol. 2, Oct. 208.
J. Song et al., "Mid-infrared pulses generated from the mixing output of an amplified, dual-wavelength Ti:sapphire system", Optics Letters, vol. 27, No. 3, Feb. 2002.
F. Blanchard et al., "Improved terahertz two-color plasma sources pumped by high intensity laser beam", Optics Express 6044, vol. 17, No. 8, Apr. 13, 2009.
R. A. Kaindl et al., "Generation, shaping, and characterization of intense femtosecond pulses tunable from 3 to 20 μm", J. Opt. Soc. Am. B/vol. 17, No. 12, Dec. 2000.

* cited by examiner

M: Mirror
DM: Dichroic mirror
CM: Concave mirror

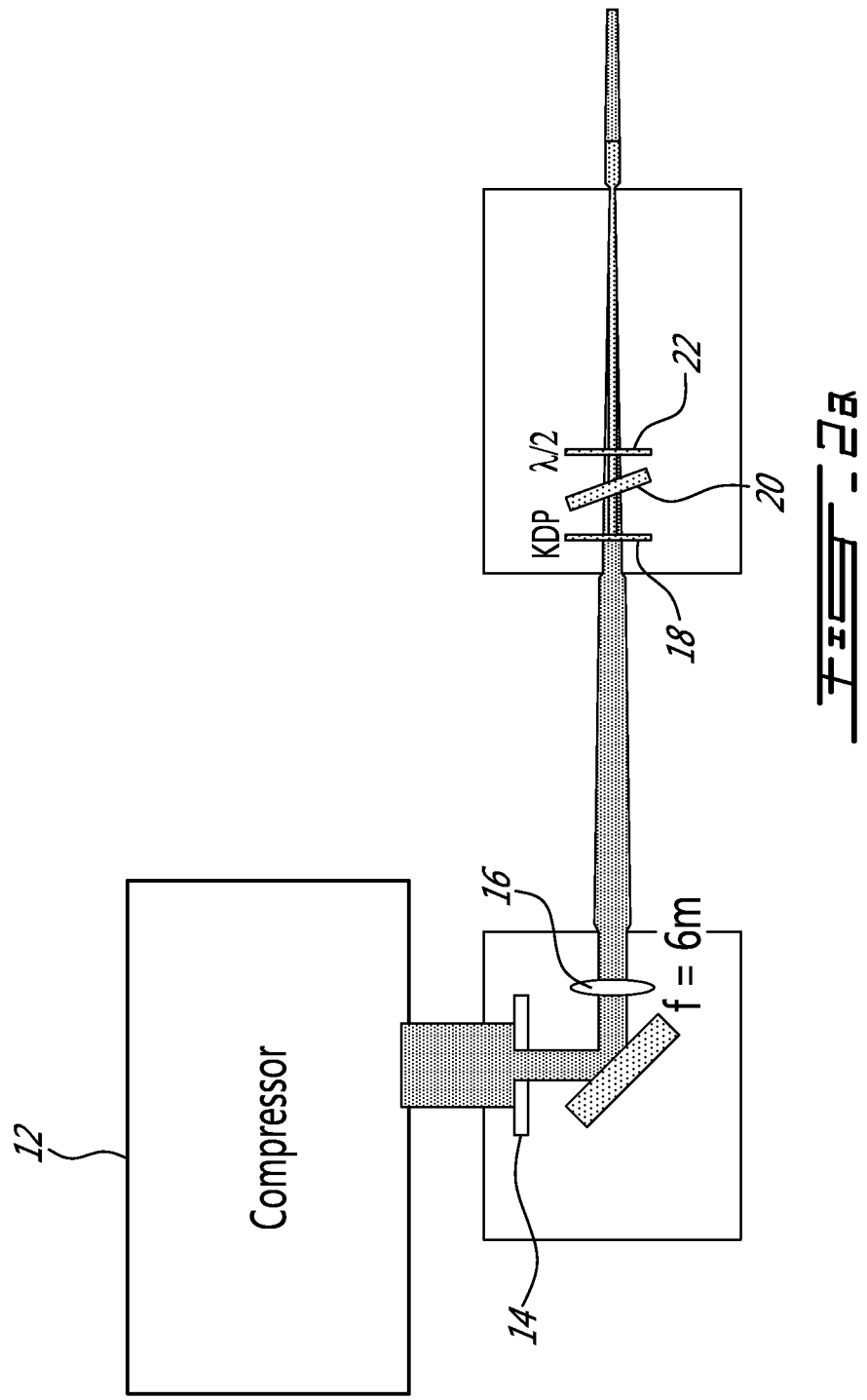

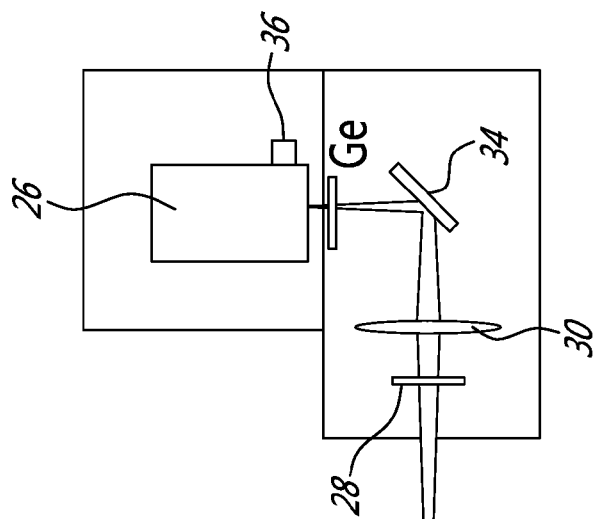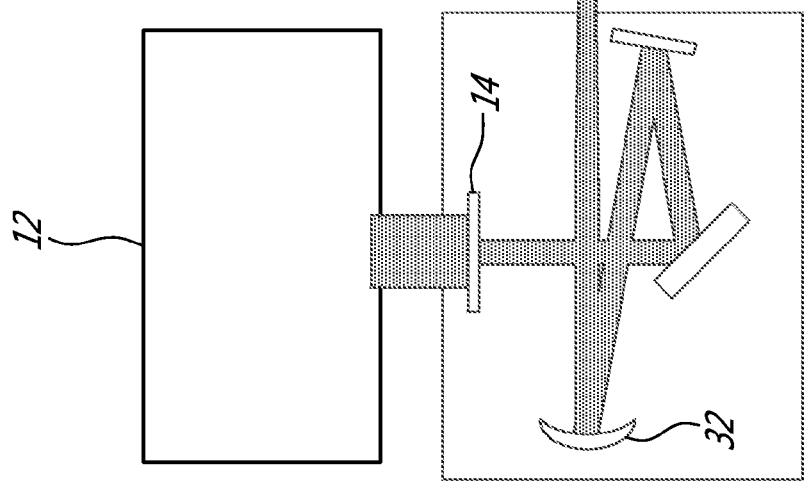
FIG-4

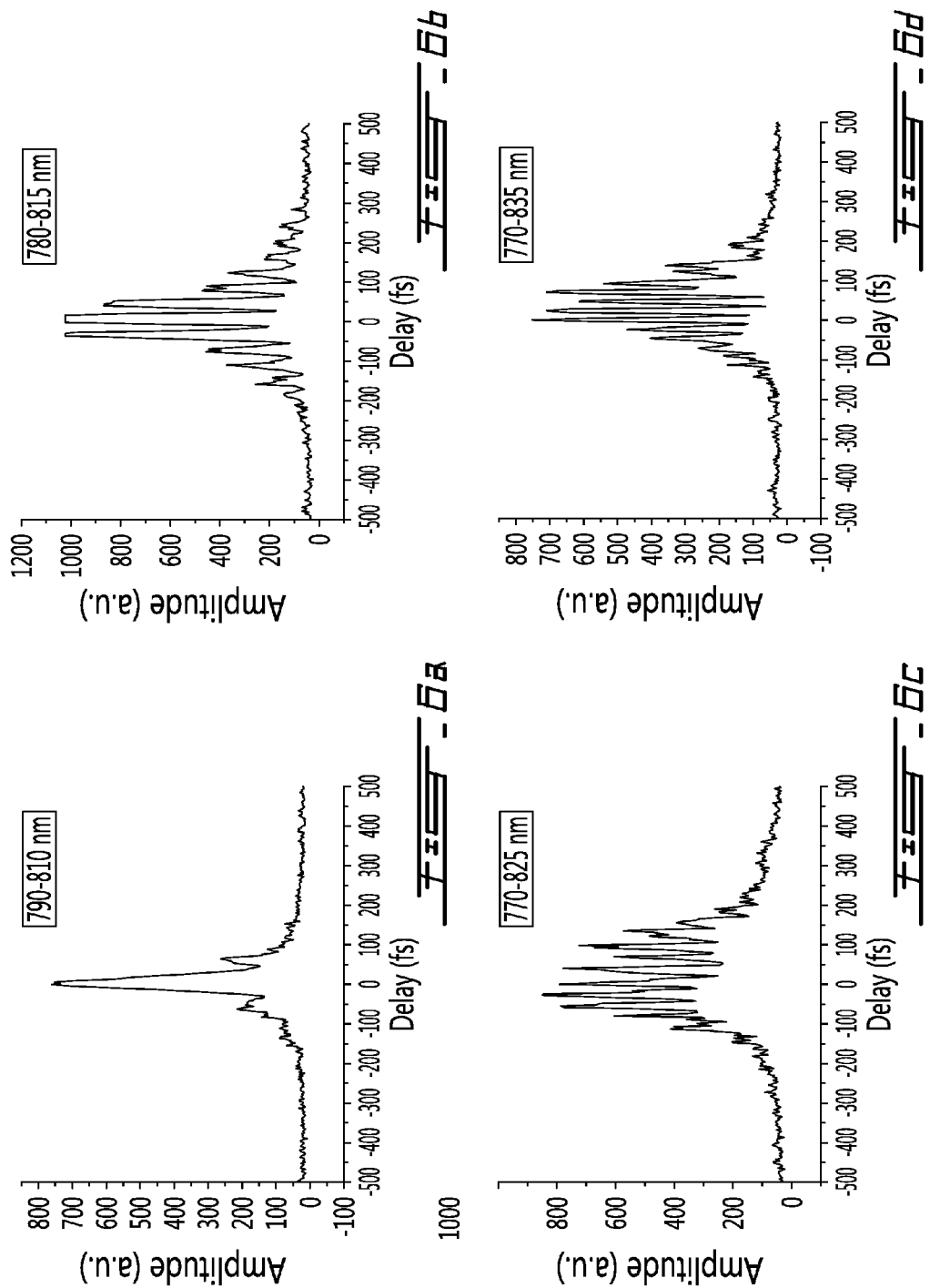

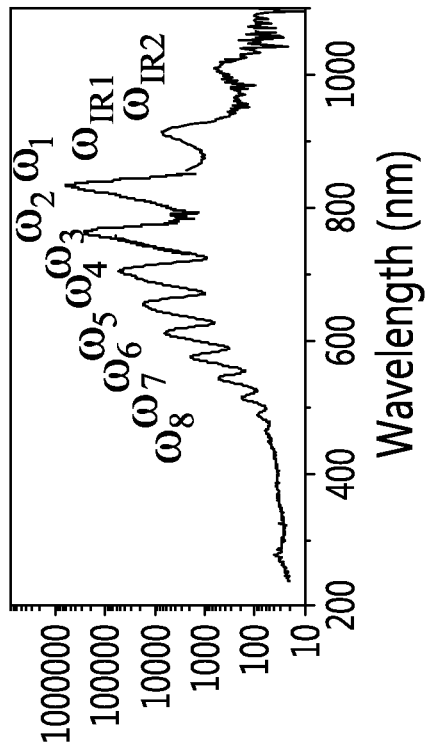

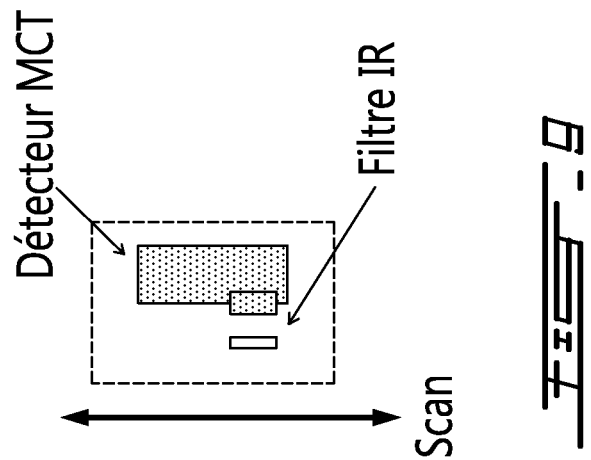

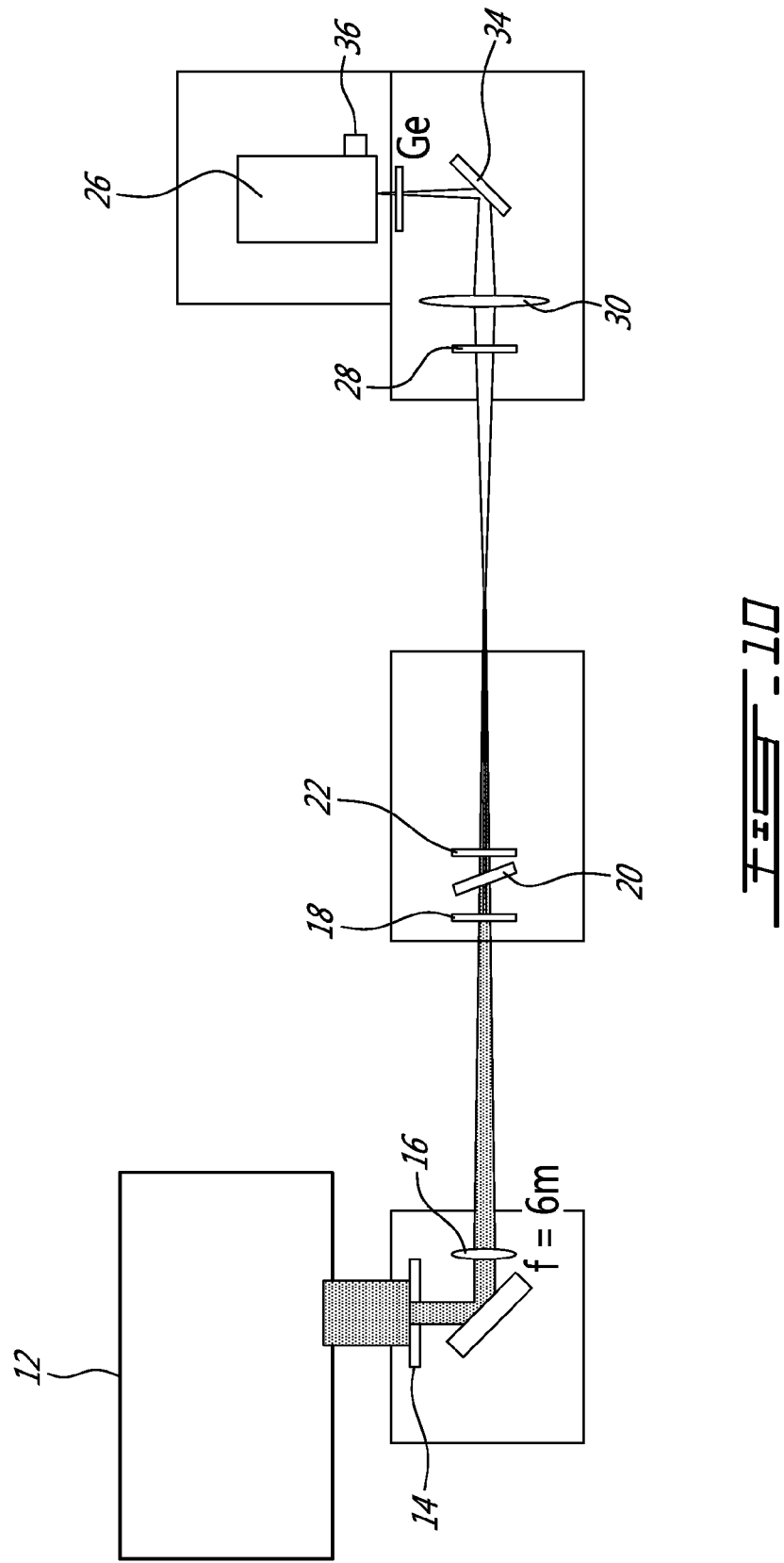

SYSTEM AND METHOD FOR AGILE REMOTE GENERATION OF A BROADBAND TUNABLE SHORT-PULSE EMISSION

CROSS REFERENCE TO RELATED APPLICATIONS

This application claims benefit, under 35 U.S.C. §119(e), of U.S. provisional application Ser. No. 61/466,580, filed on Mar. 23, 2011. All documents above are incorporated herein in their entirety by reference.

FIELD OF THE INVENTION

The present invention relates to a system and a method for generation of a broadband tunable short-pulsed source. More specifically, the present invention is concerned with a system and a method for remote generation of a broadband tunable short-pulse emission using spectrally shaped laser beam.

BACKGROUND OF THE INVENTION

The generation of sources of radiation in the ultraviolet, visible, infrared and up to the terahertz, at a distance, by nonlinear optical interaction or photocurrent generation of two, or multiple, short pulses is extremely sensible to spatial and temporal overlap of the pulses in the interaction medium. The occurrence and efficiency of the generation process is highly dependent on the ability to respect superposition conditions of the two beams, which may be complex, especially if the interaction takes place at long distance or/and at high intensities.

A current approach in nonlinear optical interaction, through four-wave mixing between two pulses of slightly different wavelengths for example, is based on splitting a laser beam into two different arms, in which one pulse is frequency doubled and the second harmonic recombines with the other fundamental pulse in a filament where the difference in frequency results in IR radiation (see FIG. 1). A first one of the arms includes a delay line, which can be made by mirrors (M) on a translation stage for instance, in order to achieve temporal overlap of the two beams.

A limitation in current systems and methods is the instability of the UV, VIS, IR and/or THz source generation due to the difficulty of using an interferometer for spatial-temporal superposition of two-color pulses. As well known to people in the art, in such a configuration, the precise alignment of both arms is critical and even if they seem exactly collinear in the range of the setup, the spatial overlap decreases as the distance increases. Also, vibrations and atmospheric density fluctuations greatly reduce the distance where the spatial-temporal overlap can be produced, typically to a few meters, and causes large fluctuation of the generated optical source, be it a UV, VIS, IR, or a THz source. Another limitation is due to the use of dichroic mirrors that divide and recombine the beams because they work only for a given laser configuration and need to be replaced for different input parameters such as the pulse wavelength, requiring further alignments.

There is still a need in the art for a system and a method to spatially and temporally overlap multiple-color pulses for long distance tunable UV, VIS, IR and/or THz source.

SUMMARY OF THE INVENTION

More specifically, in accordance with the present invention, there is provided a method for agile remote generation of a broadband tunable short-pulse emission, comprising generating multiple-color pulses directly at the output of a laser amplifier by using a pulse shaper, and mixing the pulses at a distance in a multiple-color filament, in a nonlinear optic medium.

There is provided a method of generation of an optical source on a range of distance from a laser system, comprising modulating a single beam of a large spectrum laser into colinear pulses, selecting at least two collinear pulses and combining the selected pulses at a distance in a multiple-color filament, in a nonlinear optical medium.

There is further provided a system for agile remote generation of a broadband tunable short-pulse emission in a non linear optical medium, comprising a laser amplifier unit comprising a pulse shaper for a collinear amplification of the laser beam.

Other objects, advantages and features of the present invention will become more apparent upon reading of the following non-restrictive description of specific embodiments thereof, given by way of example only with reference to the accompanying drawings

BRIEF DESCRIPTION OF THE DRAWINGS

In the appended drawings:

FIG. 4 shows an experimental set for a cascaded four-wave-mixing;

FIG. 6 show pulses trains obtained with the spectra of FIG. 5 and with a perfect temporal superposition of the two initial pulses;

FIG. 7b) shows a cascaded four-wave-mixing for the third laser configuration;

FIG. 9 shows a set up for measuring the spatial profile of the IR emission according to an embodiment of an aspect of the present invention;

FIG. 10 shows an optical setup for a direct four-wave-mixing;

DESCRIPTION OF EMBODIMENTS OF THE INVENTION

Figure 1B:
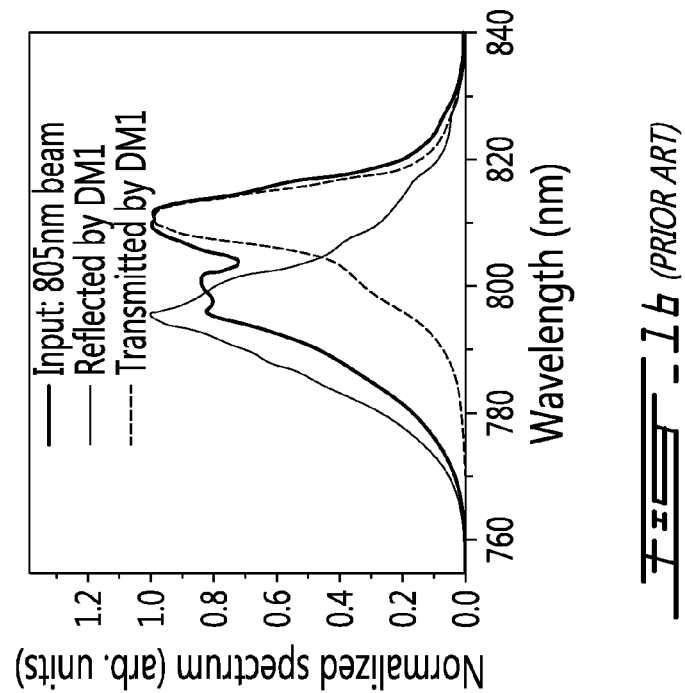
FIG. 1b) shows the spectral distribution of the laser pulses before and after the dichroic mirror DM1, as known in the prior art.
Figure 1A:
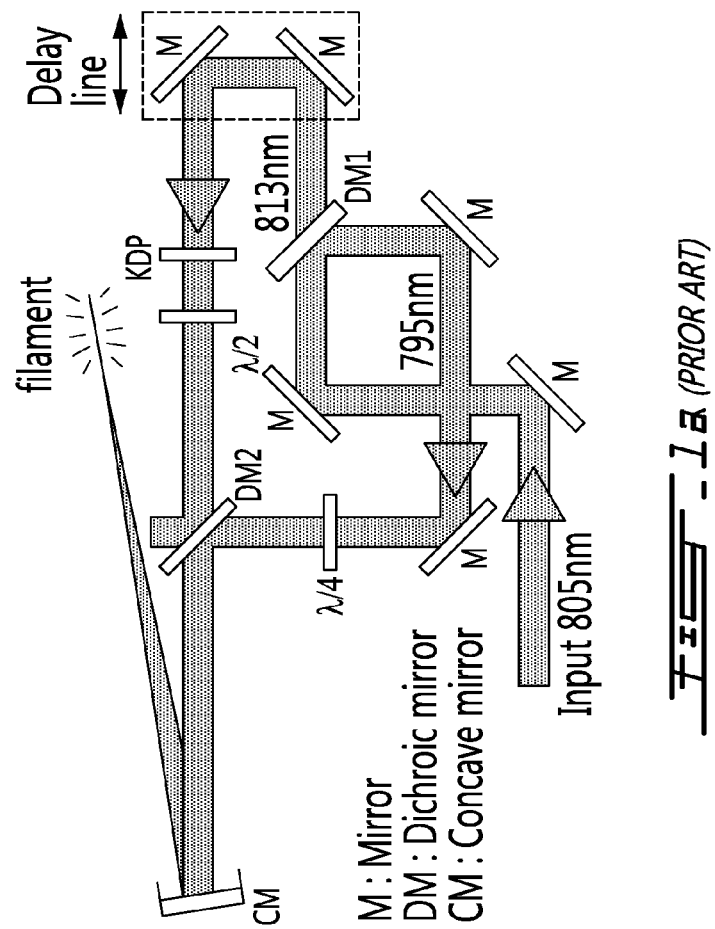
FIG. 1a) shows an experimental setup for the generation of a far-infrared pulse during filamentation in air using a laser beam split in two different beams.

Embodiments of systems and methods of the present invention will first be described, with reference to FIGS. 2 to 12, in relation to IR light.

In a first experiment, a laser system comprising a Ti:Sapphire laser and two acousto optic programmable dispersive filters (AOPDF) or Dazzler pulse shapers (Fastlite™, France) delivering 30 fs pulses at a repetition rate of 10 Hz was used. The combination of two AOPDFs allows increased control over the laser spectrum, including amplitude and phase. By using a radio frequency (RF) synthesizer, the AOPDF can be viewed as a filter with programmable transfer function in the spectral domain.

In the laser system, a first AOPDF filter was placed after a stretcher and was used to compensate for the dispersion through the laser chain in order to get the shortest pulse out of a compressor. A second filter AOPDE was placed inside a regenerative amplifier and was used to oppose gain narrowing, as, for every pass in the cavity, the central part of the spectrum is partially rejected, favoring amplification of the wings and resulting in a constant spectral gain. The effective gain was thus reduced in the center of the spectrum to yield a constant gain over a larger spectral band, the amplified spectrum thus being extended from 750 nm to 840 nm, and limited by the stretcher gratings size and the mirrors reflectivity. Only the first filter was used to amplify the two pulses.

An amplitude filter was applied to divide the oscillator spectrum into two distinctive spectra corresponding to two copropagating pulses with different wavelengths. This was done by superposition of two RF signals in the first AOPDF crystal, which allowed controlling independently each spectrum amplitude and phase and also the relative delay between the pulses by delaying the RF signals. In this experiment, the phase was kept linear so the laser pulses remained unchirped and only the delay was varied.

FIG. 2a shows an experimental setup used for generating spectra with two colors $\omega_1$ and $2\omega_2$ for IR generation by filamentation. The diameter of the beam at the output of the compressor of the laser system 12 was controlled using an iris 14. A focal lens 16 was used to focalize the pulses at the fundamental frequencies $\omega_1$ and $\omega_2$. Then, a potassium dihydrogen phosphate crystal (KDP) 18, at a distance form the lens 16, allowed increasing the efficiency of the conversion into second harmonic. As the beam was narrower at this point, the intensity was higher and the conversion rate is higher. The conversion rate was assessed by comparing the maximum of the fundamental spectrum with that of the doubled spectrum, as measured with a spectrometer (Newport OSM2-400DUV). The angles of rotation and inclination of the KDP 18 were set to double in frequency the redder pulse and avoid doubling the other pulse. A dichroic mirror 20 was used following the KDP 18 to eliminate the non-converted portion of the redder pulse.

Figure 2B:
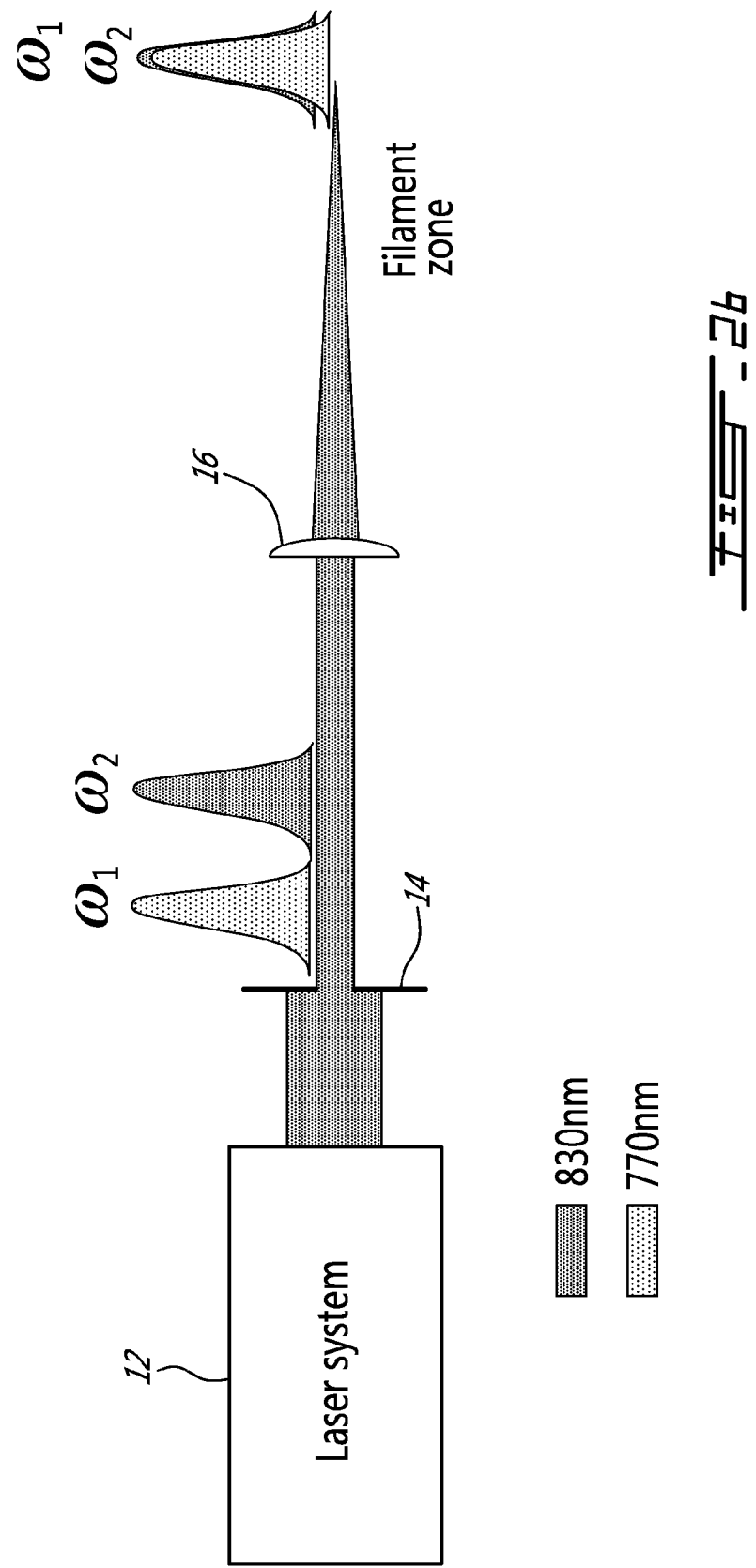
FIG. 2 show: a) an optical set up for frequency doubling of one of two initial pulses and for using them in a four-wave-mixing; b) a set up for two pulses with very close frequencies; and c) a set up for two pulses with distant frequencies, one pulse having a frequency close to the fundamental initial frequency and the other being frequency doubled.
Figure 2C:
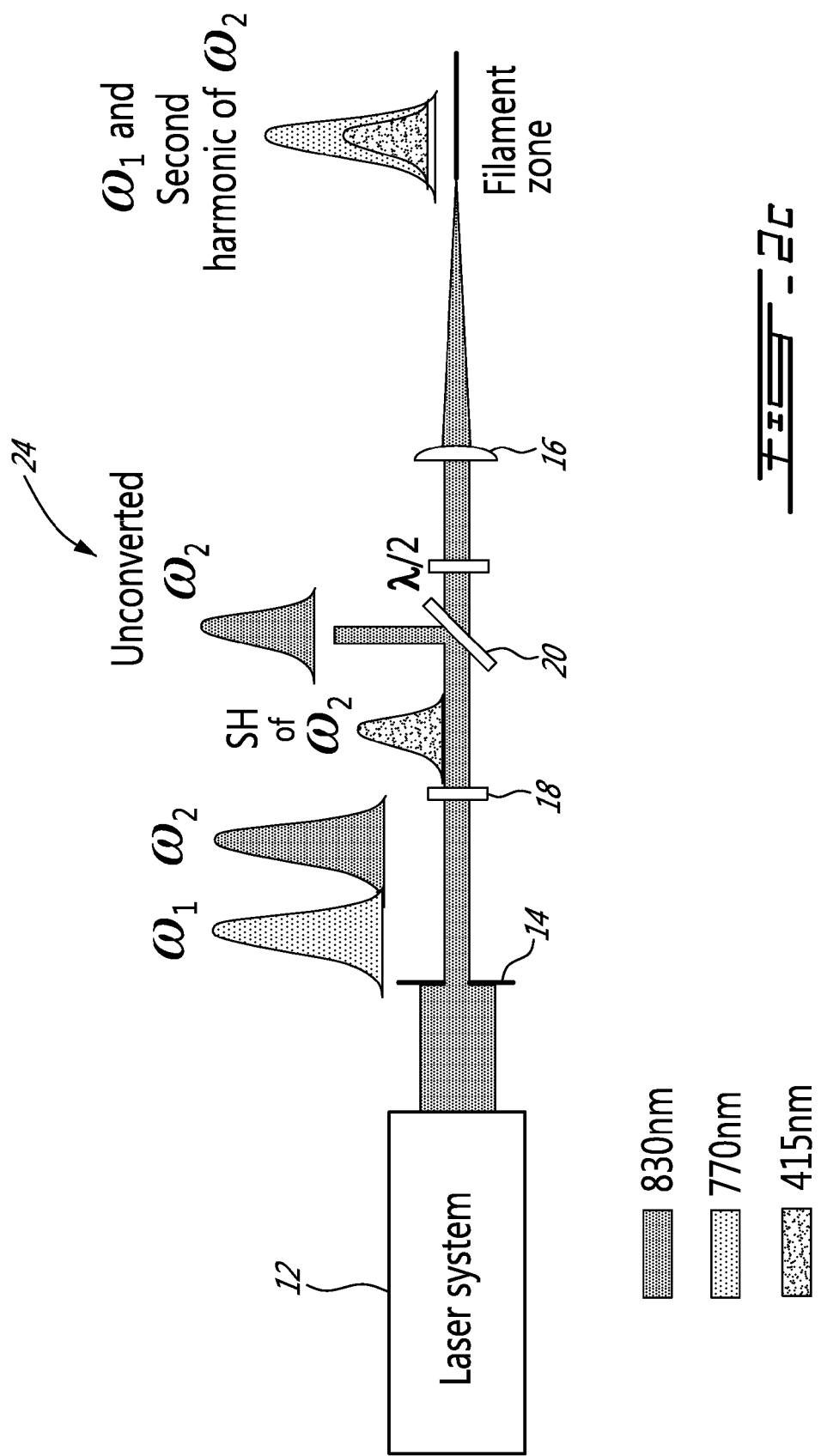

FIG. 2b shows an experimental configuration for two pulses with very close frequencies, and FIG. 2c shows an experimental configuration for two pulses with distant frequencies, one pulse having a frequency close to the fundamental initial frequency and the other being frequency doubled or otherwise adjusted by a parametric process.

The beam size emitted by the laser system 12 was reduced from 100 mm to 25 mm with the iris 14, thereby allowing to decrease the numerical aperture of the focusing optics, i.e. of the $SiO_2$ lens 16 in FIG. 2, or other optics, which was used to focalize the beams at the fundamental frequencies $\omega_1$ and $\omega_2$.

In the experimental set up shown in FIG. 2a, the synchronization in time of the two pulses was realized by adjusting the delay between the acoustic waves and was monitored with a second order autocorrelator. For a perfect synchronization in time, a train of pulses was observed and the number of pulses can be controlled by adjusting the frequency spacing between the initial pulses.

In the experimental setup shown in FIG. 2c, a 0.4 mm thick type potassium dihydrogen phosphate crystal (KDP) 18 was used to frequency double the pulse that has the longer central wavelength ($\omega_2$ in FIG. 2c). The crystal rotation was thus chosen to select the spectrum and optimize the second harmonic (SH) signal according to the phase-matching conditions.

The spectra were measured using a fiber spectrometer. Since the blue pulse has orthogonal polarization, a 800 nm half-wave plate ($\lambda/2$) 22 was inserted to turn the fundamental polarization without significantly affecting the second harmonic polarization. A dichroic mirror 20 was used to reject the unconverted fraction 24 of the long wavelength pulse $\omega_2$ because it travels faster in the different optical components. The pulse $\omega_2$ was used for second harmonic generation (SHG) but the unconverted part 24 of this pulse would produce a filament itself on which the following pulses involved in IR generation would be diffracted.

Finally, the energy in each configuration was adjusted, for example to 10 mJ in the present case for practical purposes, but similar results were obtained at various energies, just after the focusing optics, i.e. the $SiO_2$ lens 16 in FIG. 2, and the beam was focused in air. The choice of a $SiO_2$ lens instead of a focusing mirror was appropriate because chromatic aberration results in a shorter focal length for the blue pulse. Since the IR pulse undergoes self-focusing and is focused closer relative to the geometric point, the use of a lens can help to improve spatial overlap for the interaction. Nevertheless, optimizing the phase-matching conditions during the interaction remains a difficult task since it is not possible to control each pulse divergence before and inside the filament.

After the filament, the visible part of the spectrum was measured using an integration sphere and a fiber spectrometer. A silicon wafer was placed in front of the beam to filter the light under 1 µm wavelength and a 6 inch diameter NaCl lens was used to collect the remaining beam, which was sent to a monochromator where the signal was detected by two different IR photodiodes to cover the IR bandwidth up to 14 µm wavelength. Spectral overlap between the two spectrometers and the different detectors insured continuity and the measured IR spectra are shown in FIG. 3.

In the case of FIG. 2b, in order to adjust the delay between the pulses, the monochromator was set for the expected wavelength and the delay was modified to maximize the signal. No signal could be detected except for a time window corresponding to about 200 fs, which was in agreement with the pulses duration of about 100 fs. The signal was verified at different wavelengths to ensure that delay zero was the same for any wavelength and that the spectrum was not shifting when changing delay. A 1 mm microscope slide was also inserted just before the filament and a signal drop was observed at 4.5 µm wavelength, which could be completely retrieved by changing the delay by about 120 fs, corresponding to the approximate delay introduced between 400 nm and 800 nm pulses in the glass plate. In comparison, inserting a sapphire plate just after the filament zone had not effect on the detected signal except for the Fresnel losses. This observation demonstrates that the interaction takes place because of temporal overlap within the filament which extends over about 1.5 meters. However, it was not possible to further isolate the interaction zone because the filament would have damaged the materials.

Figures 3A, 3B:
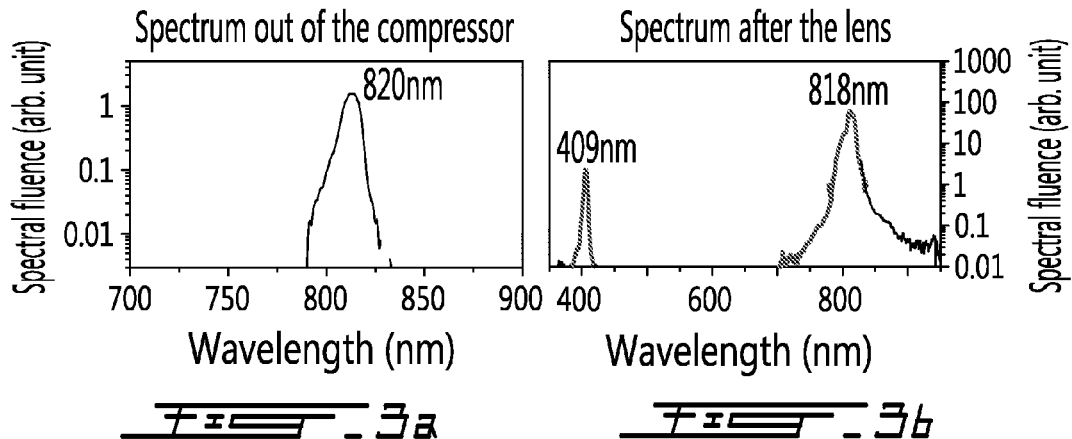
FIGS. 3a), c) and e) show spectra out of the laser system, i.e. fundamental spectra.
FIGS. 3b), d) and f) show the corresponding spectra after the KDP and the dichroic mirror lens before filamentation.

FIG. 3 show different laser configurations (FIGS. 3a, c and e), and the corresponding spectra resulting from frequency doubling a selected portion of the laser spectra.

In the case of a single pulse configuration, as shown for the first spectral configuration in FIG. 3a, it was possible to generate two pulses, as shown in FIG. 3b. However, in this case (FIG. 3b), it was not possible in the actual experimental setup to actively control the delay between the 818 nm and 409 nm pulses and thus the two pulses did not interact inside the filament due to dispersion in optics materials. Even if possible, the resulting radiation would be in the THz range and cannot be detected with the setup. In fact, the near IR pulse is always in front of the blue one. An extension in the IR similar to that reported for the propagation of a femtosecond pulse in the atmosphere was observed.

Figures 3C, 3D:
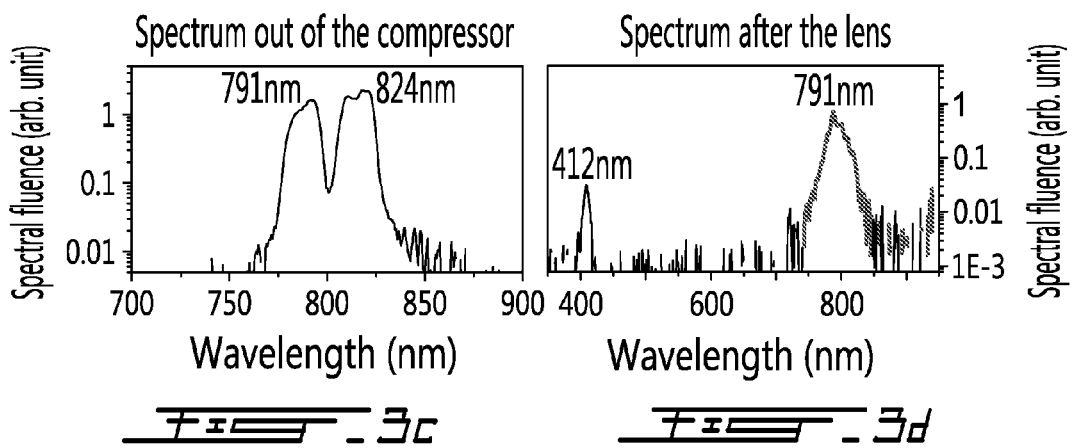
Figures 3E, 3F:
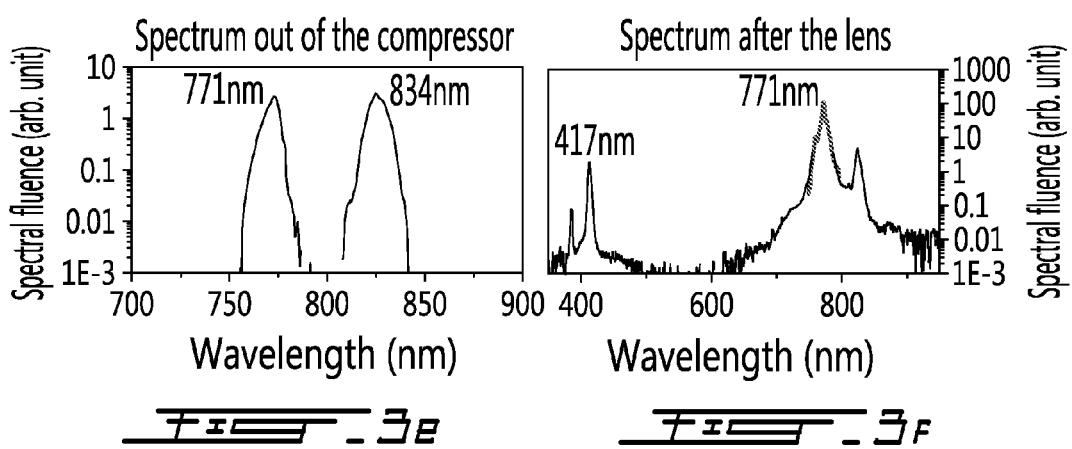

In the case of a double pulse configuration, as shown for example in FIGS. 3c and 3e, the delay could be adjusted and a very large increase of the IR generation was observed, which seemed to be preferential in the region corresponding to four-wave mixing. For instance, for the mixing between 771 nm and 417 nm (see FIG. 3f), the expected wavelength was around 5.1 µm and the signal detected in this band was at least three orders of magnitude more important than for the single pulse configuration. For the mixing between 791 nm and 412 nm (FIG. 3d), expectation was around 9.9 µm and the measured spectrum extended in the far IR up to 12 µm with a sustained signal between 7 and 10 µm that was five orders of magnitude more important than that for a single pulse configuration.

In another set of experiments, two pulses having fundamental frequencies close to 800 nm were directly mixed. The experimental set up is shown in FIG. 4. The pulses were focalized using a 5 m spherical mirror 32 in order to avoid unnecessarily inducing dispersion. A NaCl lens 30 was used to refocalize the beam emitted on the input slot of the spectrometer 26, which is imaged again on a detector at the output.

A first, InGaAs-based, detector (Thorlabs DET410) was used to detect emission between 1 and 1.7 micrometers. A second, PbSe, detector was used to detect emission from 1 to 5 micrometers. A third, liquid nitrogen cooled and HgCdTe based, detector (Infrared Associates MCT-12.5) was used to detect emission between about 2 and 14 micrometers. A silicon wafer 28 polished on both sides was used to filter all emission under 1 micrometer. A Ge wafer 34 was used to detect all emission over 2 microns.

Figures 5A, 5B, 5C, 5D:
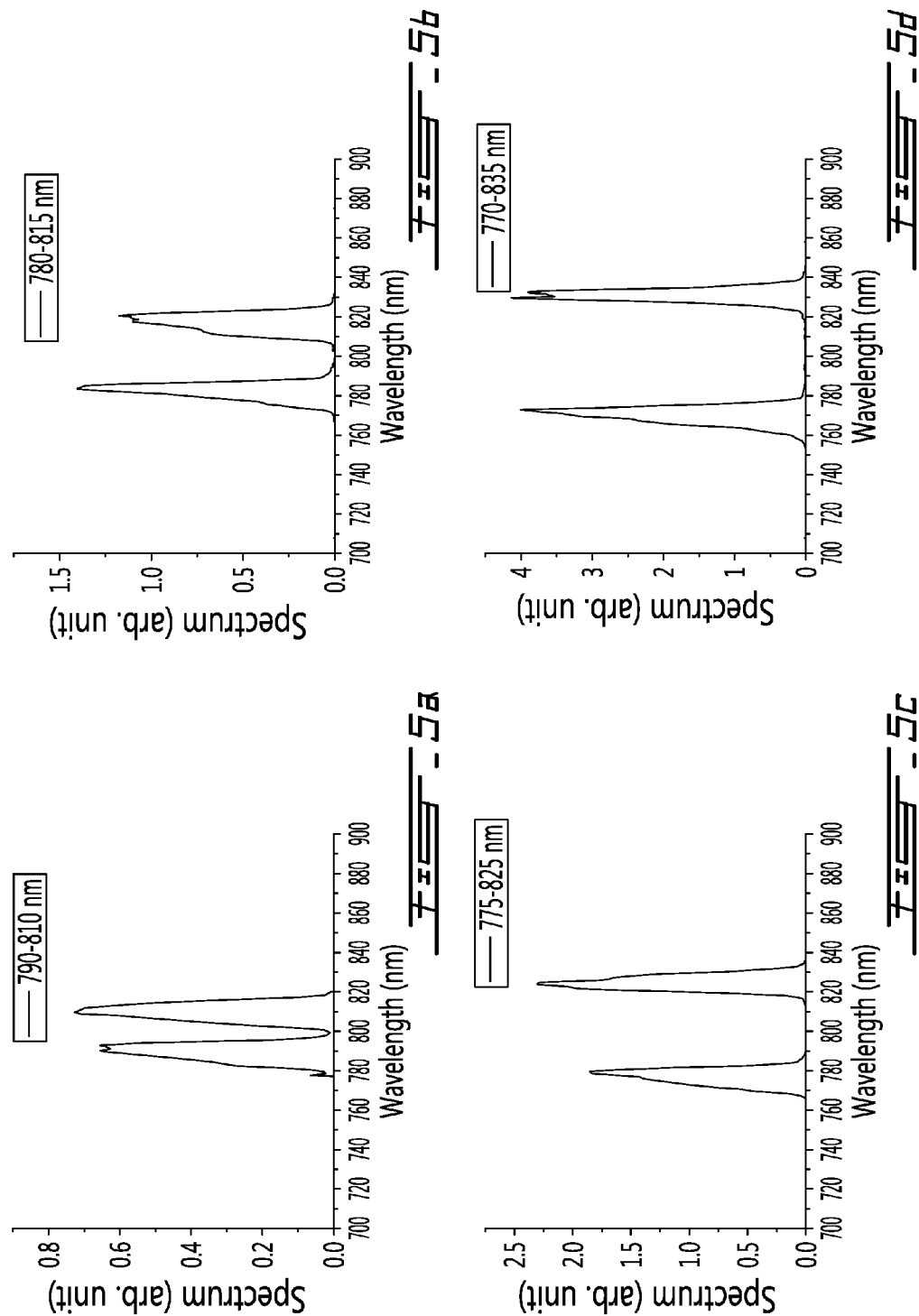
FIG. 5 show laser spectra for different two pulses configurations: a) 790-810 nm; b) 780-815 nm; c) 775-825 nm and d) 770-835 nm.

Several laser configurations were programmed using a Dazzler pulse shaper as described hereinabove (see FIG. 5). The delays for which the pulses were perfectly superimposed in time were obtained using the autocorrelator as described hereinbefore, and the pulse trains resulting from this perfect synchronization of the pulses are shown in FIG. 6 for each laser configuration.

Figure 7A:
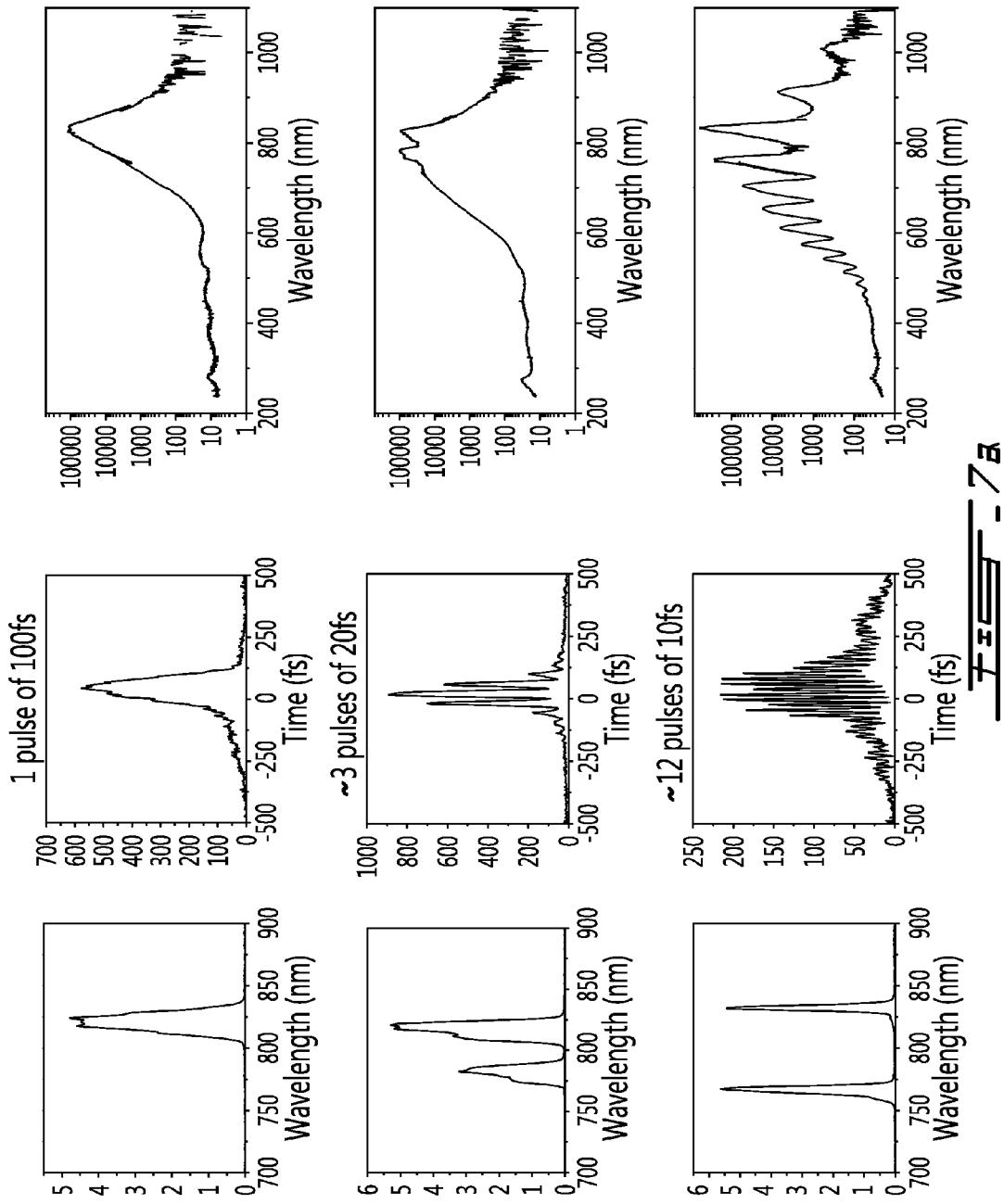
FIG. 7a) show the laser spectra before the filament (left column), autocorrelation zero delay (center column), and white light spectra obtained after the filament (right column)

The white light spectrum was measured after simply focalizing the double pulse beam. The cascaded four-waves-mixing was observed only for the configuration in which the two spectra are the more distant. The measured white light spectra are shown in FIG. 7a. FIG. 7a (right column) show white light spectra for different laser configurations and a laser energy of 10 mJ. Intensity peaks were observed in the white light spectrum of the third laser configuration, which probably correspond to cascaded four-wave-mixing (see FIG. 7b). The wavelengths of the intensity peaks correspond to values calculated according to the four-wave-mixing model.

Table I below shows the conversion rate for each configuration within the different spectral bands. Conversion in the visible and close IR seem to be favored by the third laser configuration, for which the spectra are the most distant.

TABLE I

|  | Total conversion | 400-700 nm | 900-1100 nm |
|---|---|---|---|
| Configuration 1 | 57% | 0.3% | 0.2% |
| Configuration 2 | 63% | 5.5% | 0.2% |
| Configuration 3 | 54% | 10.5% | 1.0% |

For each laser configuration, the spectrum covering UV/IS/IR/NIR/FIR was measured using detectors as mentioned hereinabove. Moreover, for each configuration, and at different energies, the signal was measured directly on a detector for different wavelengths, with different filters, in order to compare in a relative way the efficiency of IR generation as a function of energy and configuration. Finally, the spatial distribution was measured for different configurations by moving the detector transversally relative to the IR beam with different filters.

Figure 8A:
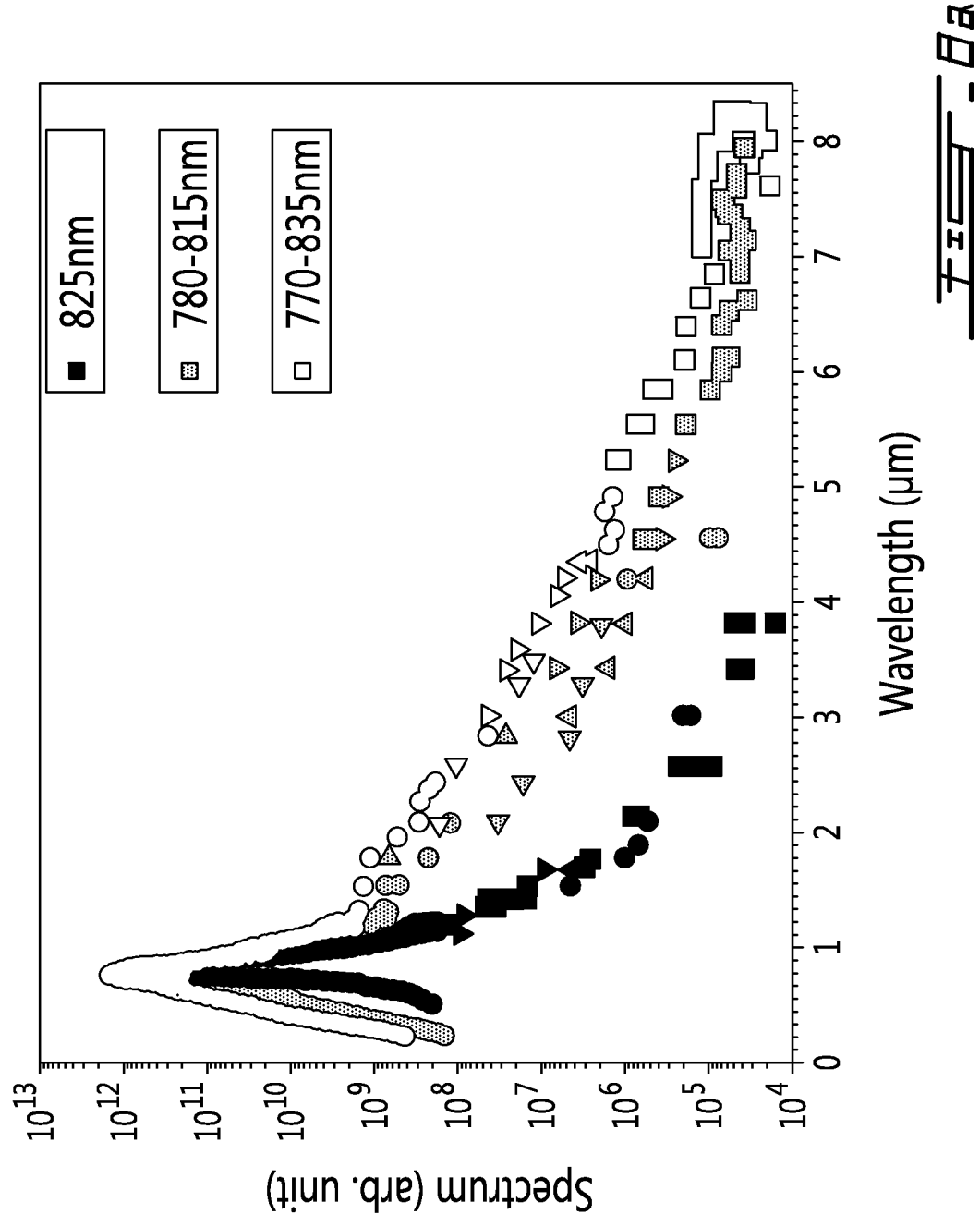
FIG. 8 show spectra measured with a simple pulse (825 nm) and with two color mixes: a) complete spectra; and b-d): zooms on UV, VIS and NIR.
Figures 8B, 8C, 8D:
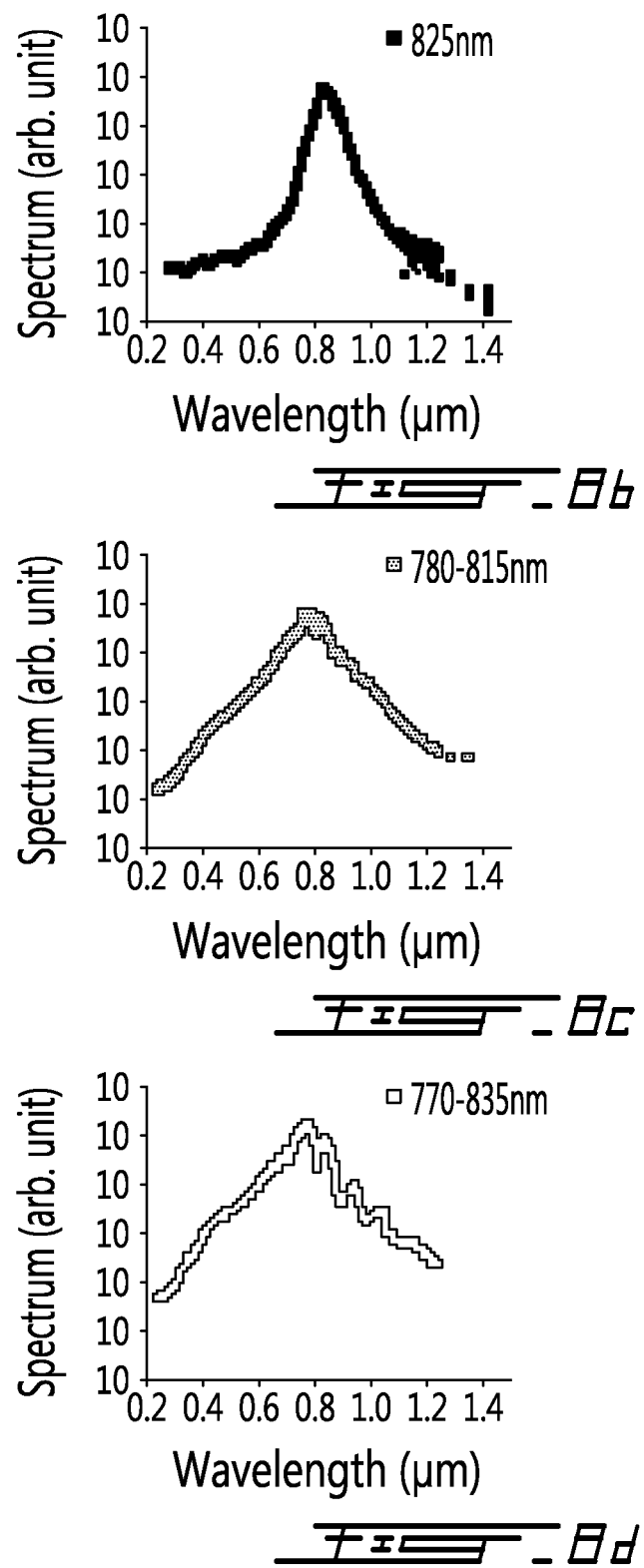

FIG. 8 shows three spectra obtained for an energy of 15 mJ and a simple pulse (825 nm), for a mixing of colors 780-815 nm and 770-835 nm, in conditions of perfect temporal synchronization. A notable increase in IR emission is seen, as well as a spreading of the spectrum towards the visible and modulations. The spatial profile of the IR emission was measured after the filament for different wavelengths and for each configuration, at a laser energy of 25 mJ, using a measurement method illustrated in FIG. 9. The detector was transversally moved along a ruler so as to obtain the profiles. The observations confirmed that conversion in the IR and the generation of more distant components in the IR seem more efficient for configuration in which the spectra are more distant one from the other.

In the case of filamentation with one pulse (color), a conical emission for IR emission was mainly observed. This emission shows a divergence of about 40-50 mrad for the range of wavelengths between 8 and 10 microns. In contrast, by modulating the initial laser spectrum, the IR emission was observed mainly on the axis, within an angle of +/−15 mrad in the range of wavelengths between 3 and 10 microns. The generated IR beam was thus less divergent.

FIG. 10 shows a set up used to induce filamentation with two wavelengths close to 800 nm and 400 nm (fundamental and second harmonic), and to generate IR emission. The lens 16 was selected to focalize the beams and maintain sufficient space after the filament for measurement of the spectrum. The dichroic mirror 20 positioned after the KDP 28 is placed before the half wave wafer 22 so as to eliminate pulse used to generate the second harmonic, which is necessary as this pulse may be ahead of the two other pulses and create a plasma that would prevent them from correctly mixing together, for example by making them diffract. This mirror 20 is in a dialectic material which operates at 45 degrees. By placing it at an angle of about 20 to 30 degrees, it allows reflecting only the undesired spectrum. Then, a half wave plate 22 at 800 nm was used to turn the polarization of IR and orient it as the second harmonic. During these experiments, the energy of the main beam was adjusted to obtain 10 mJ behind the mirror 20 that eliminates the reddest of the fundamental spectra. The second harmonic was thus contained within the energy measure.

In order to confirm that the IR signal really came from the interaction between the two pulses in the filament, for example that the pulses did not interact during propagation through the dichroic mirror, a number of tests were performed, to ensure. First, by modifying the delay of the 770 nm by about 100 fs, the IR signal was lost, which confirmed that the interaction depends on temporal superposition. In order to confirm the location of the interaction, a microscope plate (Corning 0215) was positioned on the optical path after the filament, and the signal was unchanged. This plate is used to introduce a delay between the read and blue pulses due to dispersion. When the same plate was positioned directly before the filament, the signal was lost; the signal was retrieved by introducing an extra 120 fs delay, which confirms that the temporal superposition takes place within the filament.

Figure 11:
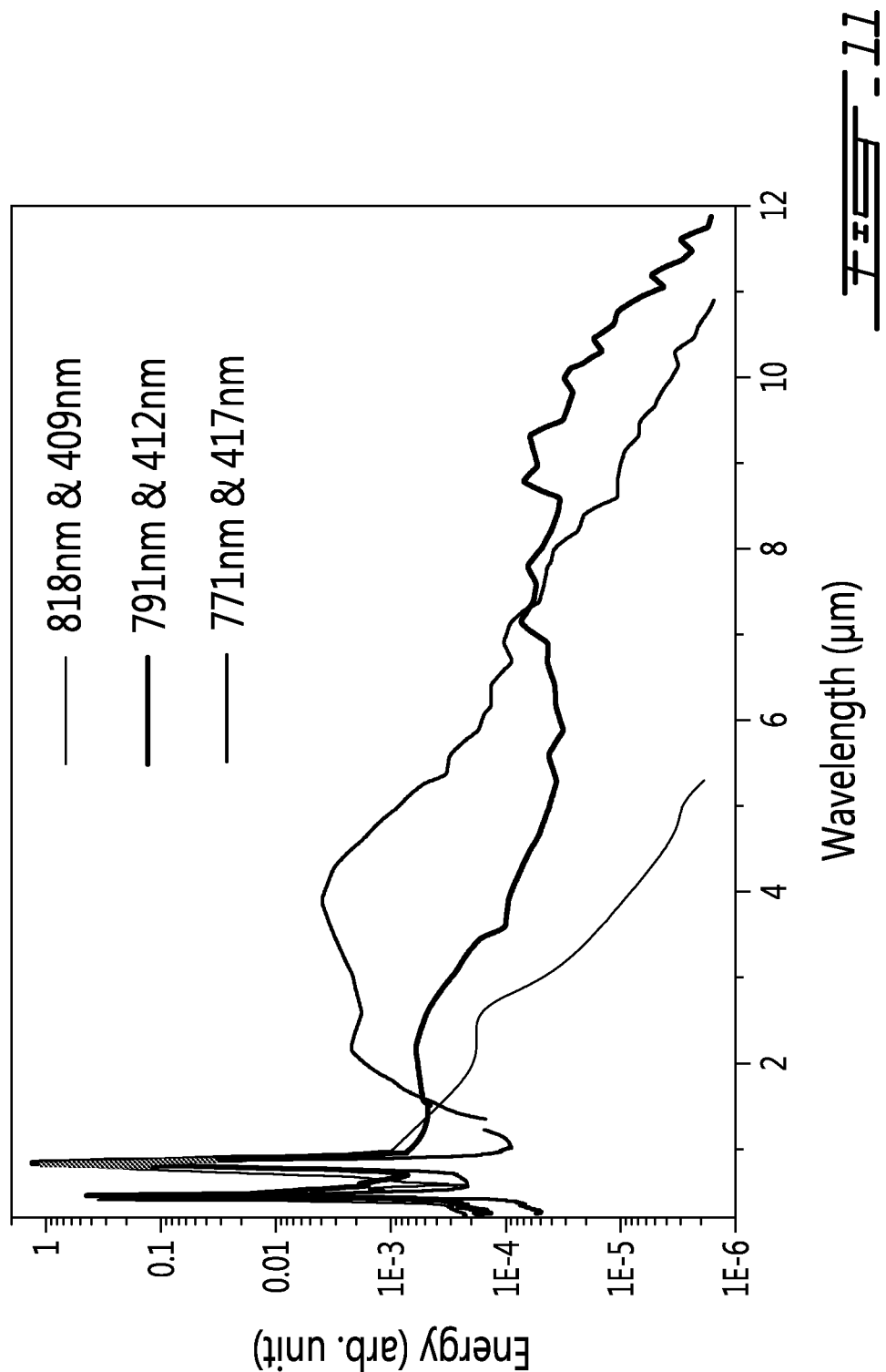
FIG. 11 shows IR spectra after the filament, at 818 nm and 409 nm; at 791 and 412 nm; and at 771 and 417 nm.

FIG. 11 shows IR spectra obtained in each configuration, after the filament, at 818 nm and 409 nm; at 791 nm and 412 nm, and at 771 nm and 417 nm. For the 818 nm spectrum, the four-wave mixing with the 409 nm was expected to yield wavelength in the THz order, i.e. non detectable with an IR spectrometer in the observed range. For the mixing of 791 nm and 412 nm, it was expected to yield an emission around 9.8 micrometers. The mixing between 771 nm and 417 nm was expected to yield an emission around 5.1 micrometers. The spectra obtained are in compliance with these expectations. It is to be noted that the bands of the laser spectrum are rather large and that a shift of about 10 nm at about 800 nm corresponds to a shift of about 100 nm at about 8 micrometers for example. Moreover, the mixing does not necessarily occur between the centers of the bands. As a result, emission is rather large in the IR.

Figures 12A, 12B:
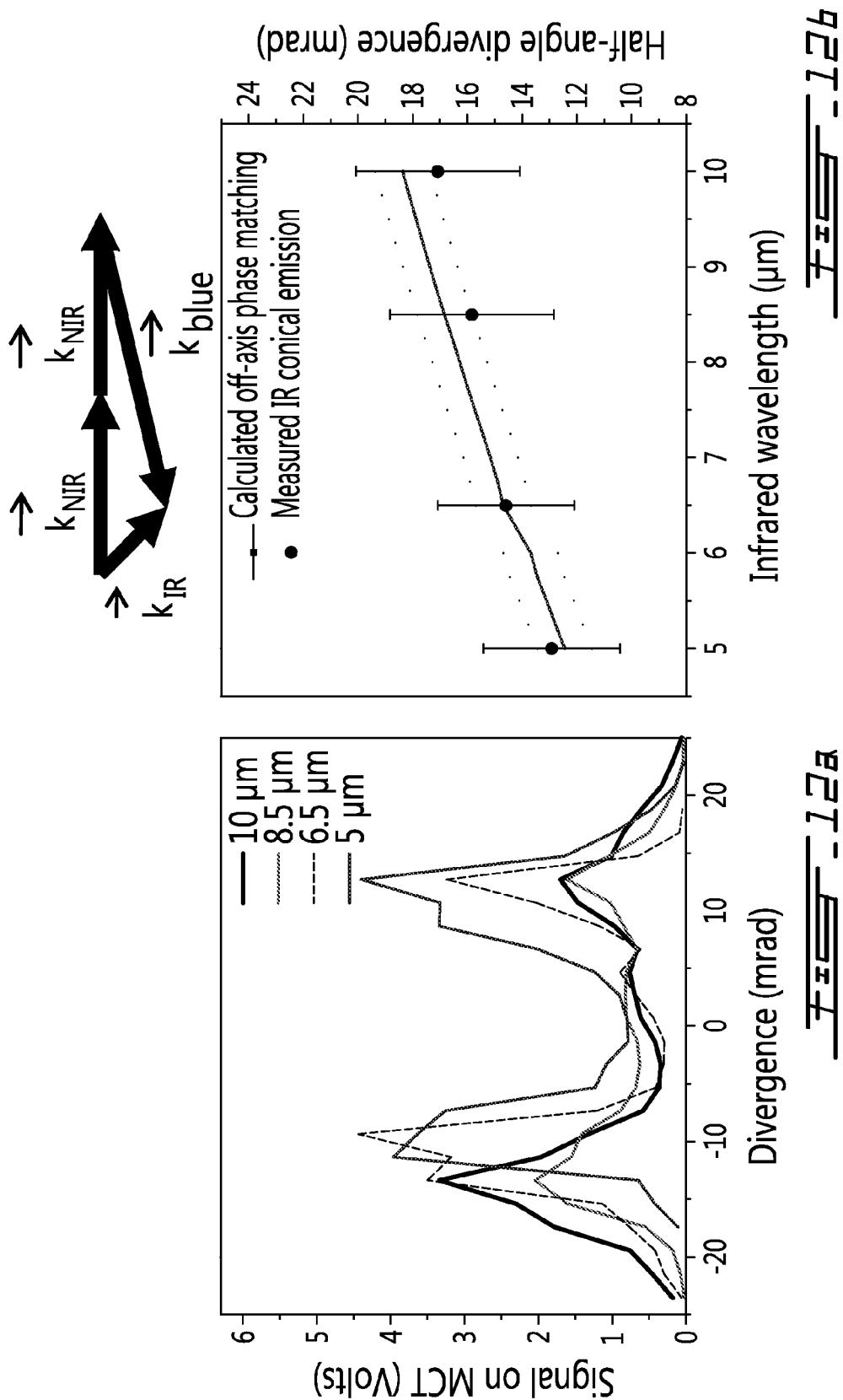
FIG. 12a) shows an IR profile measures about 10 cm behind the NaCl lens with different filters; and b) shows the expected divergence based on phase matching computations.

According to the phase-matching conditions for FWM, a conical emission of the IR was observed, which is shown in FIG. 12a for the experimental set up of FIG. 12c. The divergence was measured by moving an HgCdTe detector with appropriate filters across the beam at a given distance from the tale of the filament. To compare this conical emission with the calculated off-axis phase matching inside the filament, it was considered that the spread of wavevectors for both the red and blue pulses were within ±1 mrad relative to the propagation axis (FIG. 12b).

In conclusion, IR generation by multiple-color filamentation with the use of a pulse shaper in the laser system was thus demonstrated. The spectral emission was measured for three different double pulse configurations (See FIGS. 3b, d, f) and the IR emission could be controlled. By choosing two pulses close in wavelength, the IR emission was extended in the far IR up to 12 μm. Inversely, separating more the wavelengths resulted in enhanced emission for the mid IR. The characteristic divergence of the emission was also measured, which was between 10 and 20 mrad in agreement with the phase-matching conditions during FWM.

Amplification of two pulses by modulation of the spectral amplitude and phase was thus shown to be a simple method that enables to perform two color filamentation with a single beam. It gives the ability to finely control the pulse delay and skillfully achieve spatial and temporal overlap in the filament without separation and recombination of the laser beam.

As people in the art will appreciate, the present method and system allow overcoming problems such as synchronization of two lasers and stability of the two lasers.

The present method and system allow IR long range applications. For example, for military applications, IR may be generated at distances from 100 m to 100 Km.

In order to generate THz radiation along a similar principle, the second harmonic has to be mixed with its own fundamental pulse. However, filters do not allow controlling the delay between the second harmonic pulse and its corresponding fundamental pulse. To overcome this limitation, the laser spectrum was modulated in three different parts, the central part was frequency doubled and the blue pulse mixed with two photons having an equal and opposite wavelength difference with respect to the central wavelength, for example. The blue pulse delay could thus be controlled independently of the two other fundamental pulses, which allowed extending the tunability in the THz range. Because the blue pulse delay can be actively controlled, the second harmonic crystal can be placed before the focusing optics and this feature enables to use larger crystals and to increase the total energy involved in the process. This method also allows to actively control the relative delay between the different pulses involved in the four-wave mixing process and consequently the THz waveform.

Figure 13:
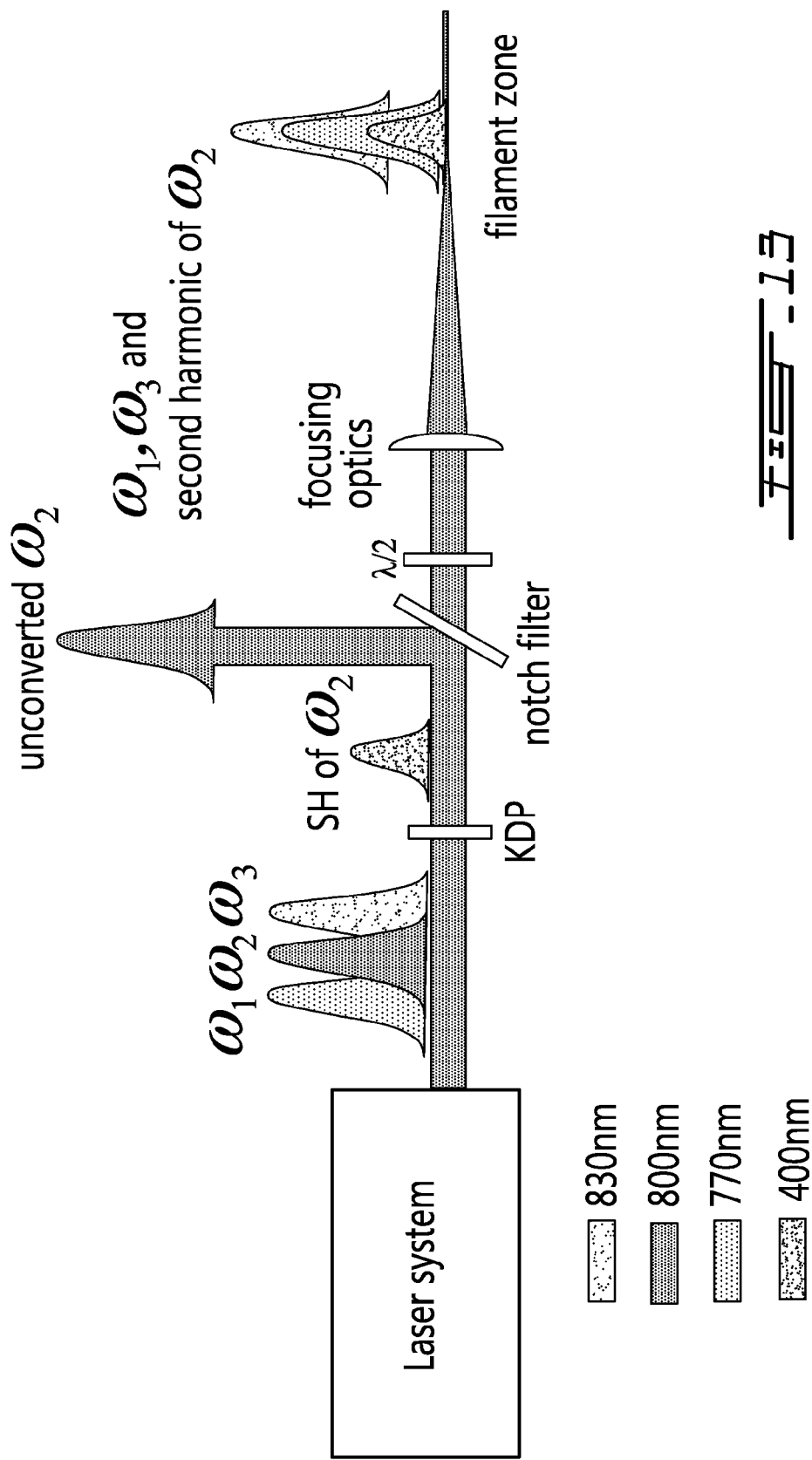
FIG. 13 shows an experimental configuration for the generation of THz radiation.
Figure 14:
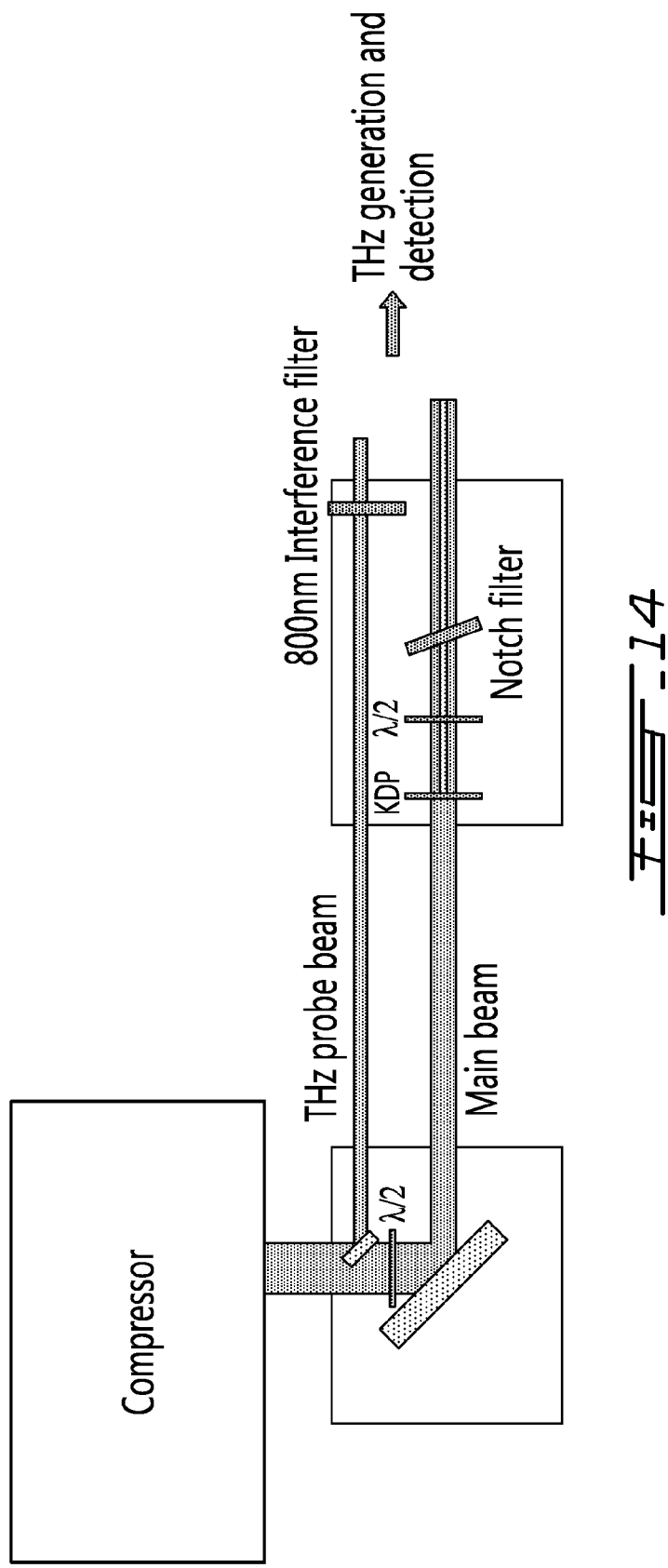
FIG. 14 shows an experimental setup for THz generation.

In an experimental configuration shown in FIGS. 13 and 14, for three pulses with distant frequencies, two pulses having a frequency close to the fundamental initial frequency and the pulse with the central frequency being frequency doubled, a 5 mm thick type potassium dihydrogen phosphate crystal (KDP) was used to frequency double the pulse at the central wavelength (800 nm). A half-wave plate (λ/2) was used to ensure a correct orientation of the polarization following the KDP crystal and a notch filter removed the 800 nm. The blue pulse delay could thus be controlled independently of the two other fundamental pulses, thereby extending the tunability of the method in the THz range. Because the blue pulse delay could be actively controlled, the second harmonic crystal could be placed before the focusing optics, which allowed using larger crystals and increasing the total energy involved in the process. This method also allowed to actively control the relative delay between the different pulses involved in the four-wave mixing process and consequently the THz waveform.

Figure 15:
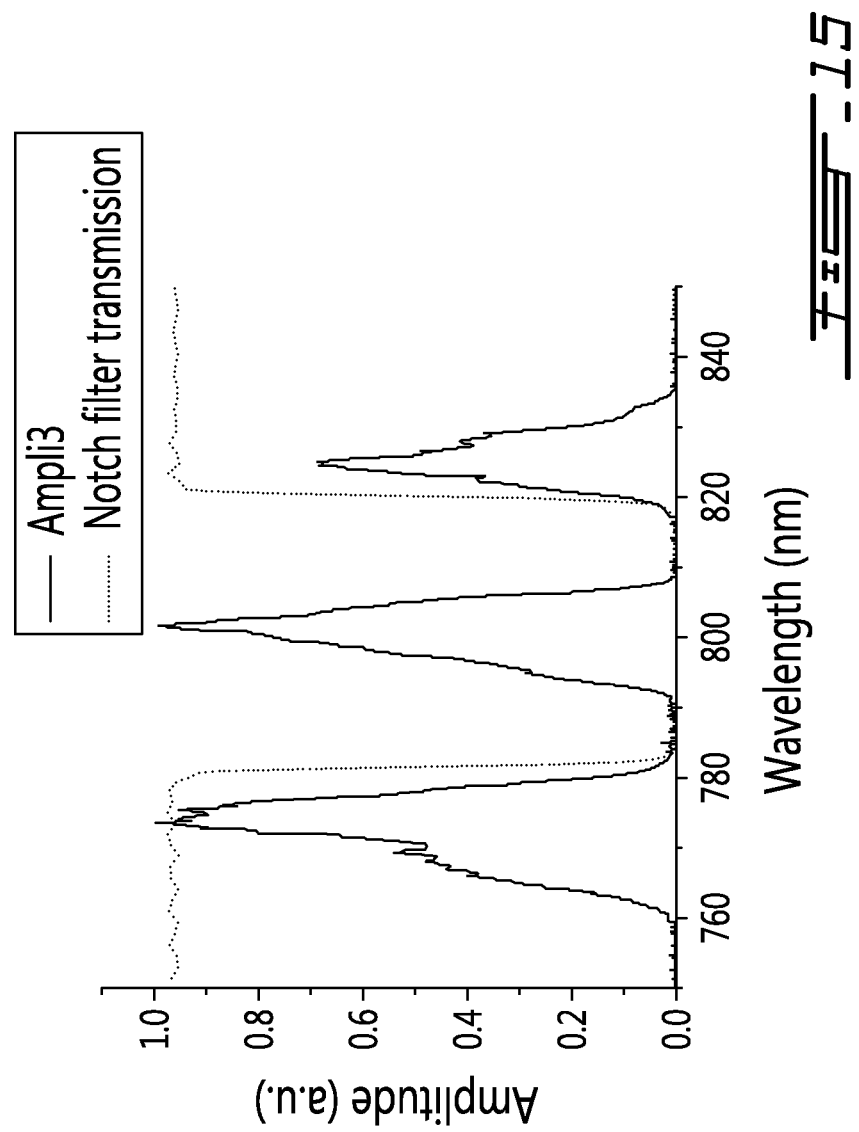
FIG. 15 shows the modulated laser spectrum at the fundamental frequency.

The laser spectrum was modulated in three different parts by applying the corresponding amplitude filter before the stretcher. The modulated spectrum is shown in FIG. 15. With an AOPDF, two independent amplitude filters could be used simultaneously and the phase control of each acoustic wave allowed temporally overlapping each spectrum. The first acoustic wave corresponded to the central part of the spectrum at 800 nm. The second acoustic wave corresponded to the remaining part of the spectrum that is the remaining two peaks at around 770 nm and 830 nm. It was possible to control any possible delay between those three pulses.

Figure 16:
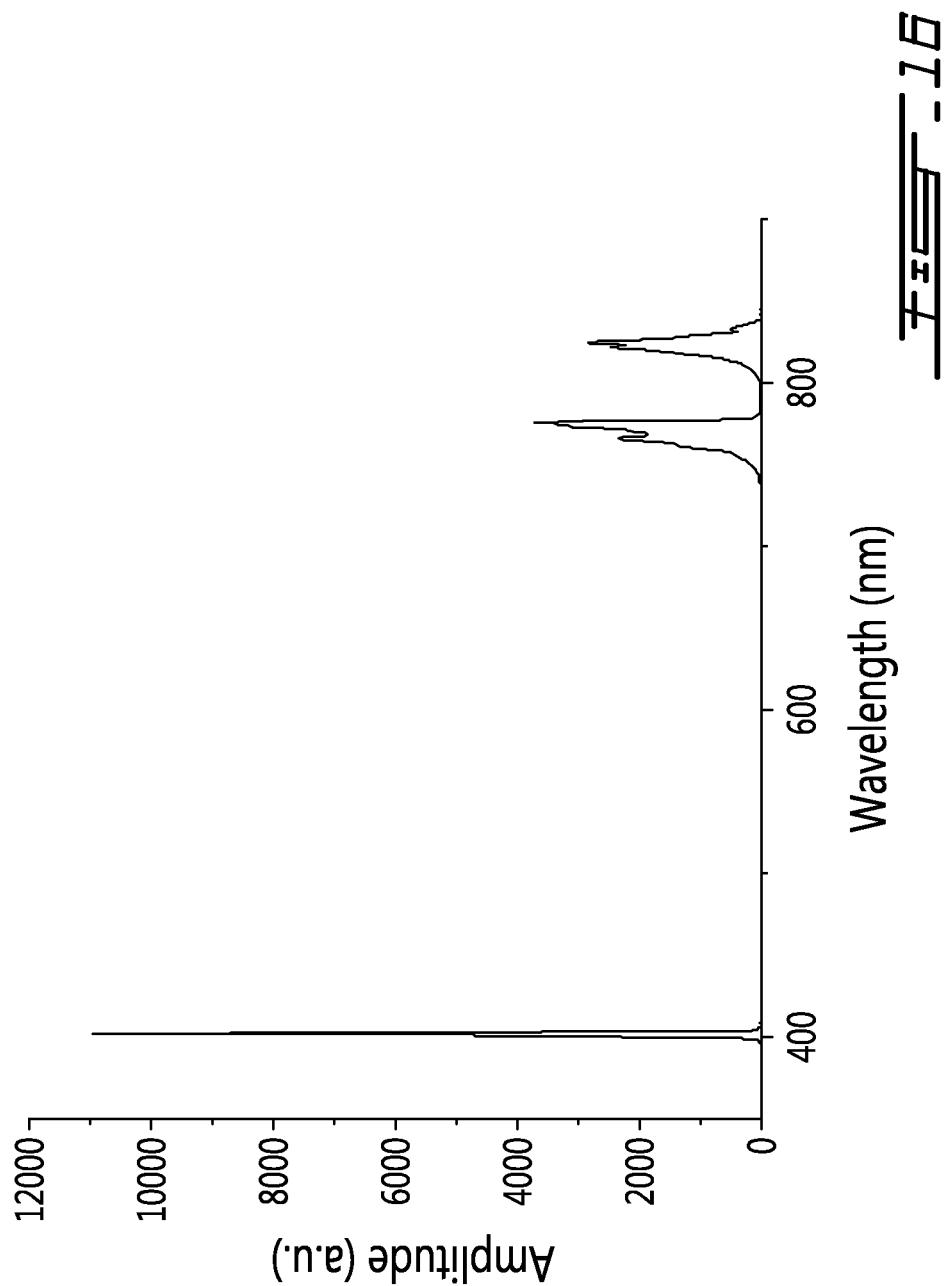
FIG. 16 shows a laser spectrum after KDP crystal and notch filter (main beam), for THz generation: $\omega_1$ (770 nm), $\omega_3$ (830 nm) and the second harmonic of $\omega_2$ (400 nm)

A suitable spectrum for THz generation is shown in FIG. 16.

Figure 17:
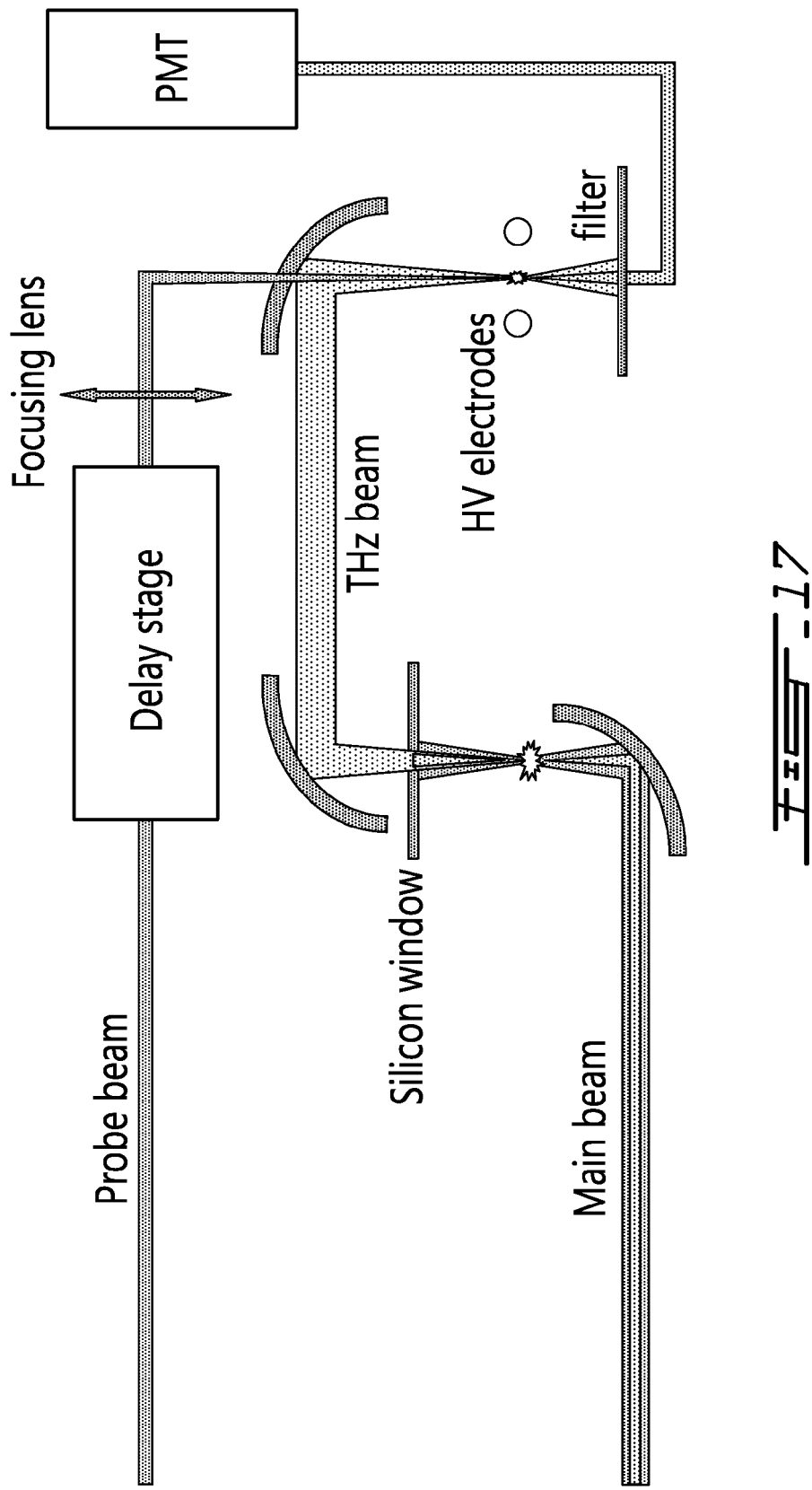
FIG. 17 shows an optical layout for THz generation and detection.

As shown in FIG. 17, the main beam was focused by an off-axis parabola and created a first plasma in which the three spectra shown in FIG. 16 mixed. A silicon window was used as a filter to insure that only the THz beam propagated toward the detection module.

Figure 18:
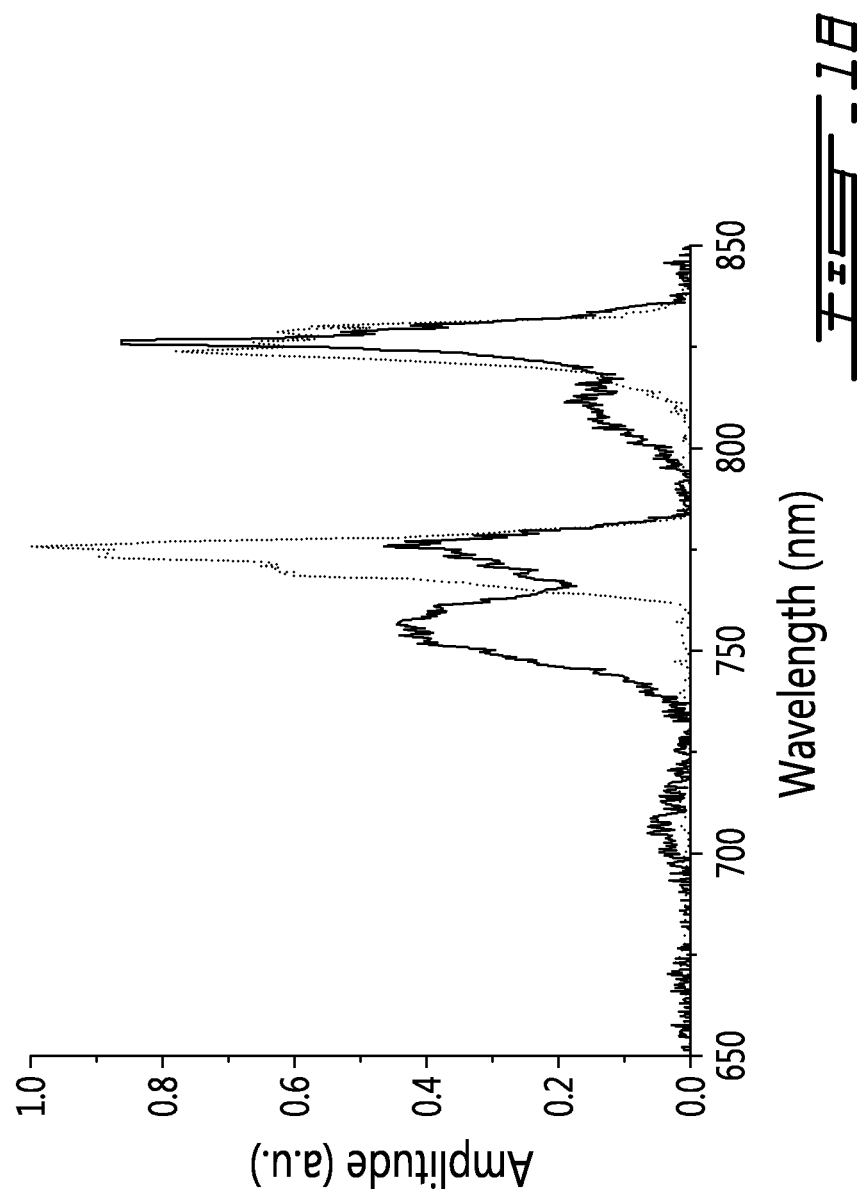
FIG. 18 shows spectra observed for two different delays between the 770 nm pulse and the 830 nm pulse: spectral broadening observed when delay was zero (solid line), and in the same conditions but for a non zero delay (dotted line)
Figure 19:
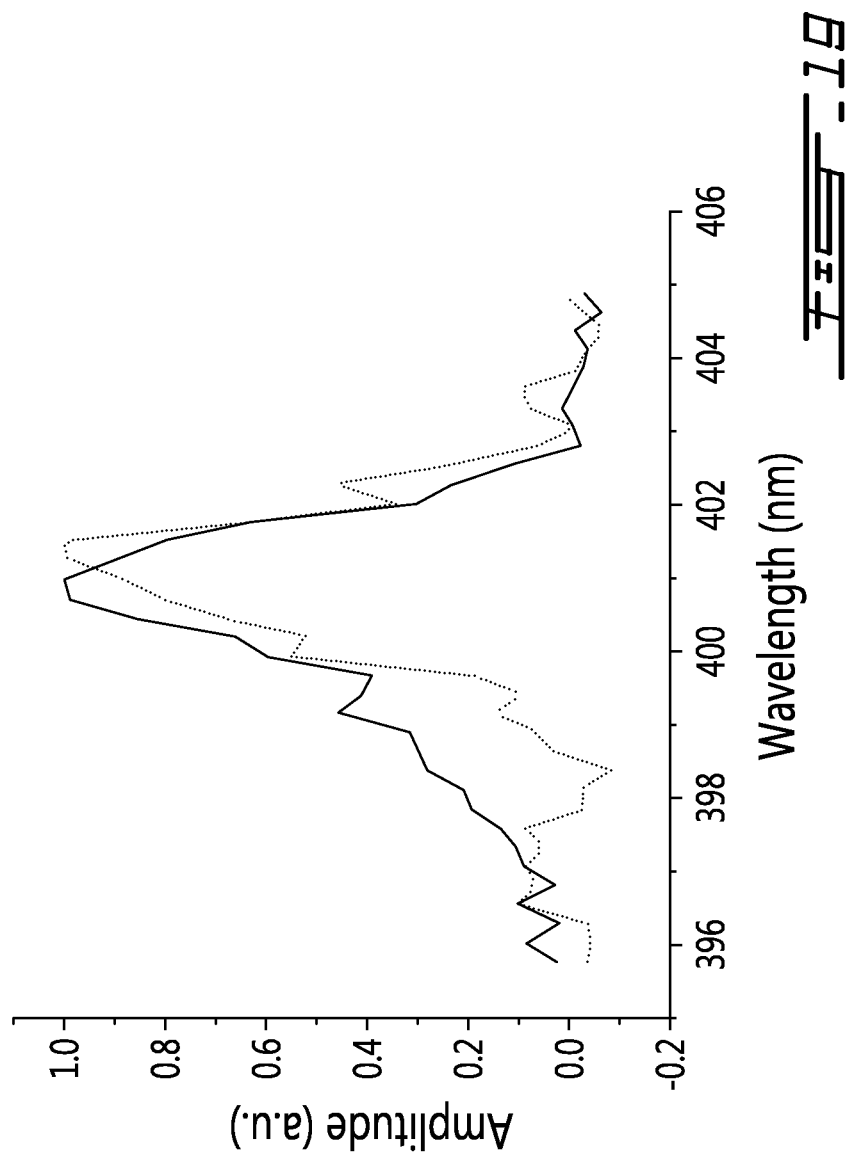
FIG. 19 shows spectra observed for two different delays between the 400 nm pulse and the overlapped 770 nm and 830 nm pulse spectral broadening observed when delay was zero (solid line)

In order to confirm temporal overlap, the fundamental spectra were observed with a conventional spectrometer. When the temporal delay between the 770 nm and the 830 nm pulses was zero, a spectral broadening could be observed after the plasma and this observation is explained by the increase of intensity when the pulses interfere. This observation was used to set the delay correctly between those two pulses, as shown in FIG. 18. The same observation was used to correctly set the delay for the 400 nm pulse (FIG. 19).

Figure 20:
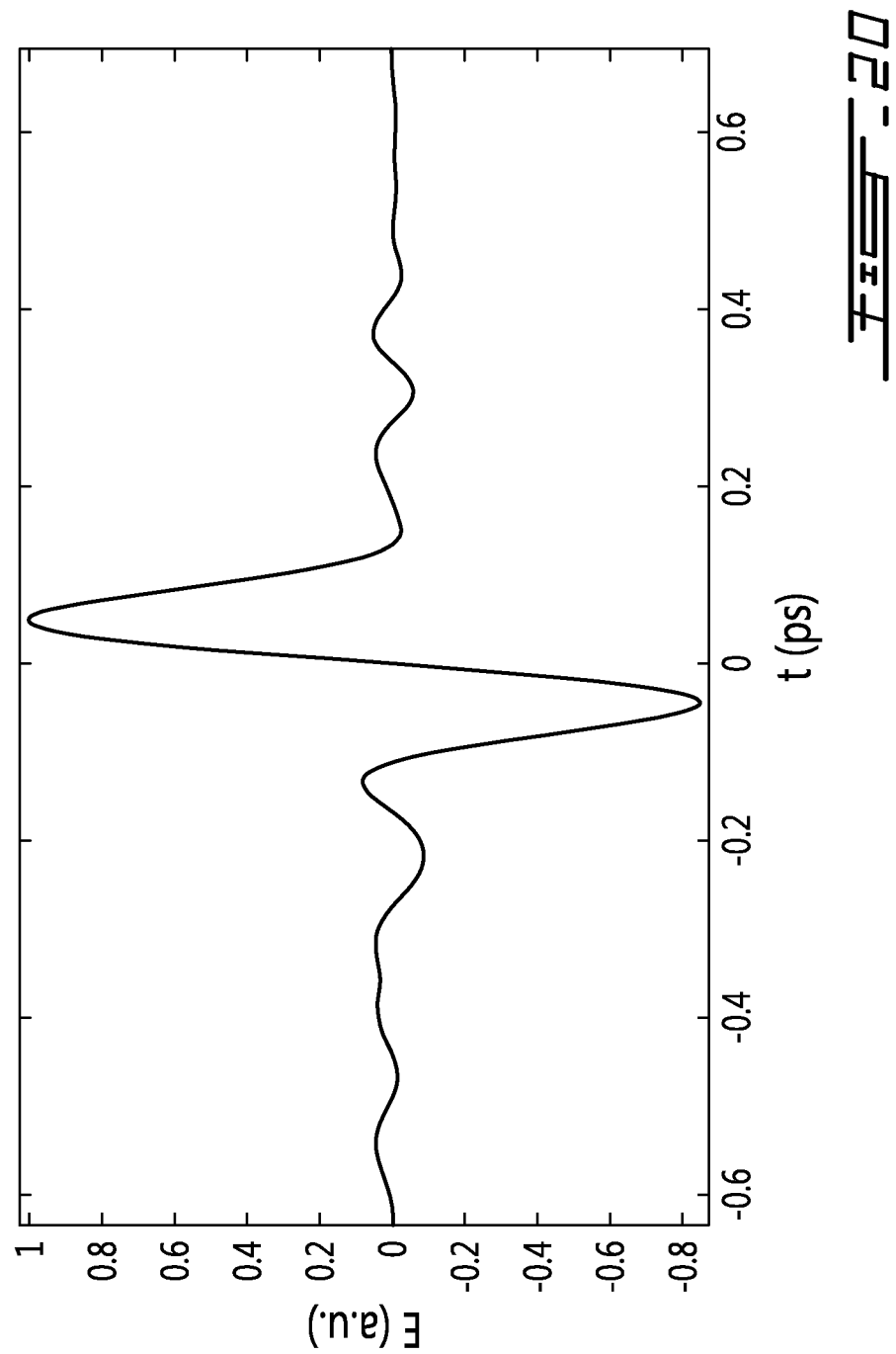
FIG. 20 shows the THz electric field generated by the four wave mixing (FWM) of 770 nm, 830 nm and 400 nm pulses.
Figure 21:
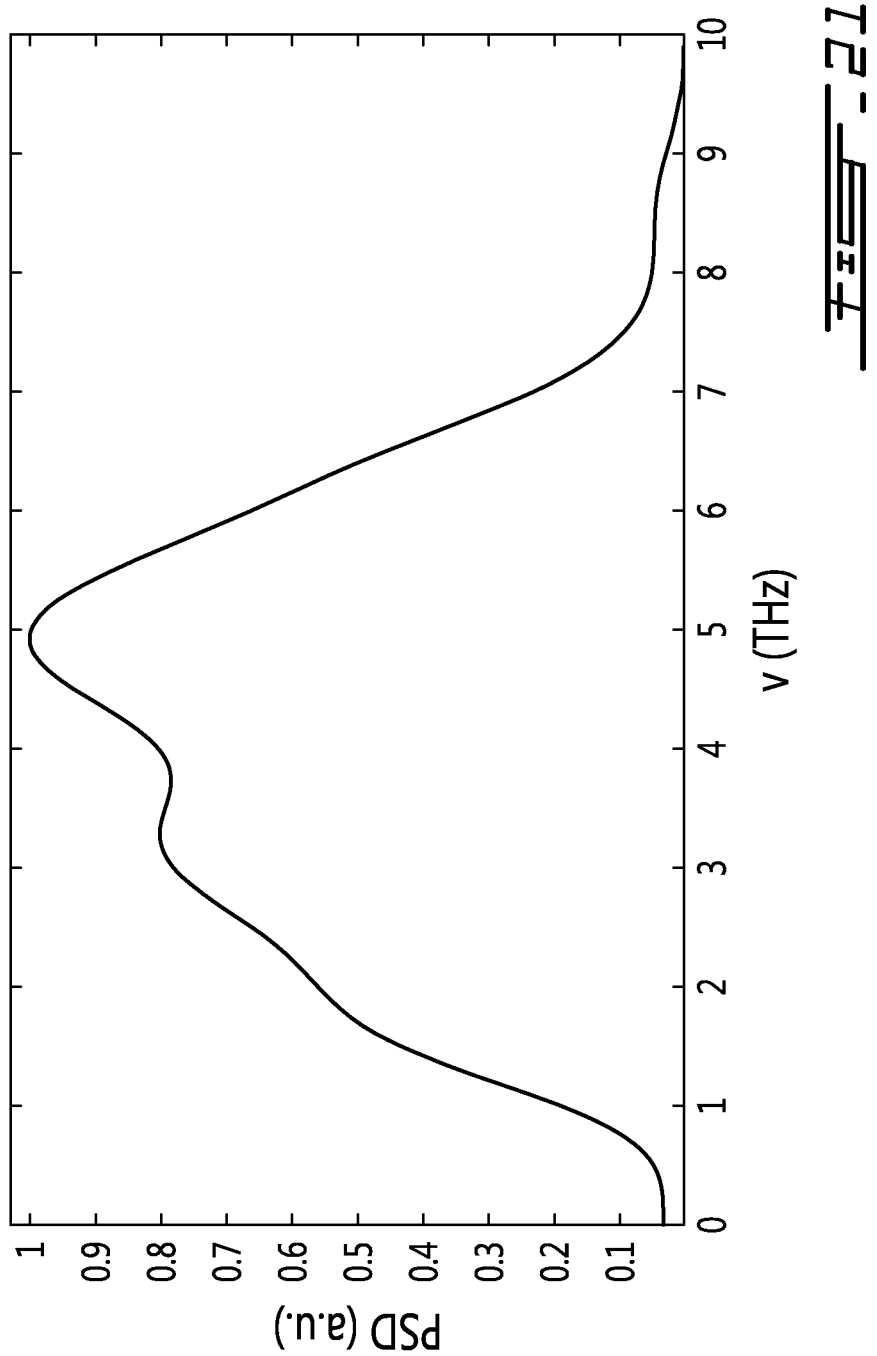
FIG. 21 shows the power spectral density inferred from the measured electric field of FIG. 20.

The temporal overlap between the three pulses was adjusted and verified using spectrometers. The coherent part of the second harmonic signal is proportional to the THz electric field amplitude so it is possible to retrieve the electric field by sweeping the delay of the probe beam. FIG. 20 shows the detected THz coherent electric field. This measurement confirms that this spectral shaping can lead to broadband THz generation, as seen in FIG. 21 where the THz spectrum inferred from the electric field (FIG. 20) has an extended bandwidth up to 10 THz.

Figure 22B:
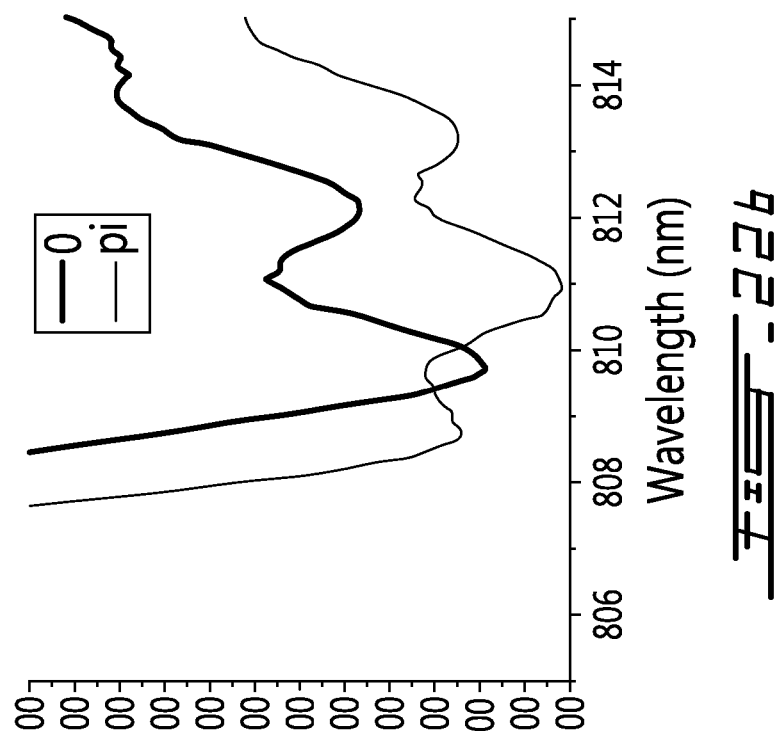
FIG. 22 show interference patterns between 800 nm pulse and 830 nm pulse for two different delays between them (a and b).
Figure 22A:
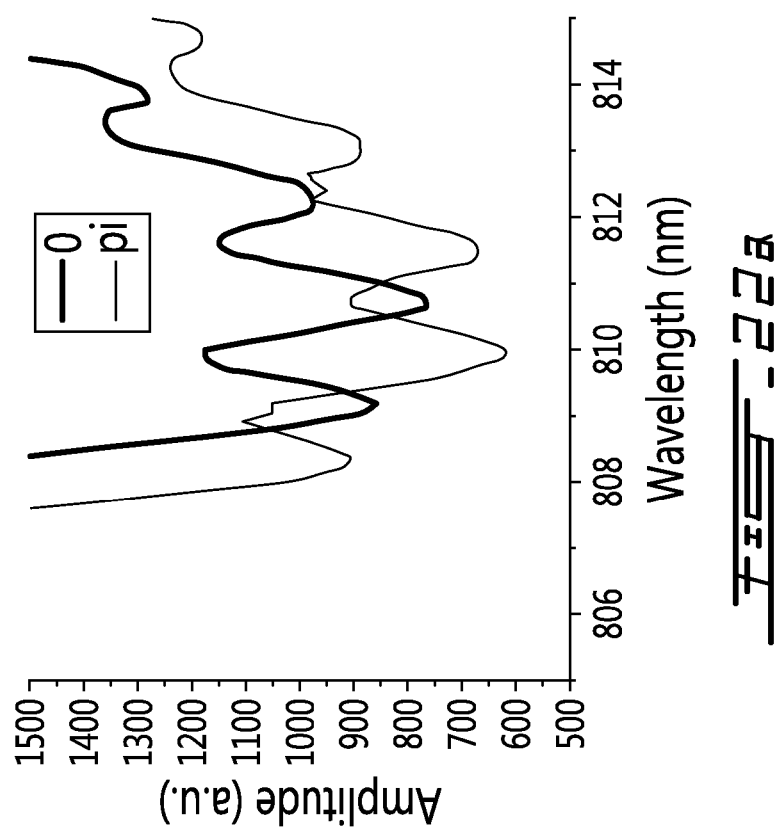

FIG. 22 show the interference patterns between 800 nm pulse and 830 nm pulse for two different delays between them (a and b), as shown by the difference in the fringes separation. The pulses were adjusted with two different relative phase in each case (see the difference for the position of the peaks in the fringes). In FIG. 22, the control of the relative phase between the 800 nm and the 830 nm pulse is demonstrated. The pulses are focused with sufficient energy and their respective spectrum broaden just enough so they spectrally overlap and the delay between them creates interference. This phase control shows that it should be possible to control the THz electric field absolute phase as shown elsewhere (see Dai, J., N. Karpowicz, and X. C. Zhang, *Coherent Polarization Control of Terahertz Waves Generated from Two-Color Laser-Induced Gas Plasma*. Physical Review Letters, 2009. 103(2): p. 023001), where the relative phase between the blue pulse and the fundamental pulse was changed by inserting a fused silica wedge pair perpendicular to the beam. In the present case, it is possible to control this parameter by changing the phase of the acoustic wave in the filter, avoiding moving parts and propagation through additional optical materials.

There is thus provided a method comprising using a pulse shaper in the spectral domain to generate multiple-color pulses directly at the output of the laser amplifier. The delay can thus be controlled directly in the spectral domain and there is no need for an optical delay line. The method allows reducing the number of optical components and insures insensitivity to alignment, vibrations and turbulence on long distance propagation and filamentation, particularly in air.

The method allows programmable and tunable interaction, since the pulse shaper is able to control the laser spectral amplitude and phase using a computer.

The present system and method are completely collinear, on short and long distances, and programmable, and allow generation of an optical source, i.e. a UV, VIS, IR and/or THz source, using multiple-color pulses interacting through nonlinear optical processes.

The present method and system allow a collinear geometry, programmable tunability from visible to THz. Pulse shaping is not limited to the fundamental spectrum. The initial spectrum may be modified using optical parametric processes. The emission can be generated at a distance with insensivity to alignment, vibrations and turbulence. The absolute phase of the generated pulses may be actively and finely controlled. The interaction zone may be any single, or combination of, non linear optical mediums (gas, liquid or solid). A range of pulse shapers, as well as of focusing optics, high or low numerical aperture, may be used. Lasers having large bandwidth or multiple band lasers may be used.

Although the present invention has been described hereinabove by way of embodiments thereof, it may be modified, without departing from the nature and teachings of the subject invention as recited herein.

REFERENCES

1. T. Fuji, T. Horio, and T. Suzuki, "Generation of 12 fs deep-ultraviolet pulses by four-wave mixing through filamentation in neon gas," Opt. Lett. 32, 2481-2483 (2007).
2. T. Fuji, and T. Suzuki, "Generation of sub-two-cycle mid-infrared pulses by four-wave mixing through filamentation in air," Opt. Lett. 32, 3330-3332 (2007).
3. J. Kasparian, R. Sauerbrey, D. Mondelain, S. Niedermeier, J. Yu, J. P. Wolf, Y. B. André, M. Franco, B. Prade, S. Tzortzakis, A. Mysyrowicz, M. Rodriguez, H. Wille, and L. Wöste, "Infrared extension of the super continuum generated by femtosecond terawatt laser pulses propagating in the atmosphere," Opt. Lett. 25, 1397-1399 (2000).
4. F. Théberge, M. Châteauneuf, V. Ross, P. Mathieu, and J. Dubois, "Ultrabroadband conical emission generated from the ultraviolet up to the far-infrared during the optical filamentation in air," Opt. Lett. 33, 2515-2517 (2008).
5. F. Théberge, N. Akozbek, W. Liu, A. Becker, and S. L. Chin, "Tunable Ultrashort Laser Pulses Generated through Filamentation in Gases," Physical Review Letters 97, 023904 (2006).
6. D. J. Cook, and R. M. Hochstrasser, "Intense terahertz pulses by four-wave rectification in air," Opt. Lett. 25, 1210-1212 (2000).
7. Y. Zhang, Y. Chen, C. Marceau, W. Liu, Z. D. Sun, S. Xu, F. Théberge, M. Châteauneuf, J. Dubois, and S. L. Chin, "Non-radially polarized THz pulse emitted from femtosecond laser filament in air," Opt. Express 16, 15483-15488 (2008).
8. F. Théberge, M. Chateauneuf, G. Roy, P. Mathieu, and J. Dubois, "Generation of tunable and broadband far-infrared laser pulses during two-color filamentation," Physical Review A 81, 033821 (2010).
9. F. Verluise, V. Laude, Z. Cheng, C. Spielmann, and P. Tournois, "Amplitude and phase control of ultrashort pulses by use of an acousto-optic programmable dispersive filter: pulse compression and shaping," Optics Letters 25, 575-577 (2000).
10. S. Watanabe, K. Midorikawa, T. Oksenhendler, D. Kaplan, P. Tournois, G. Greetham, and F. Estable, "Ultrawideband Regenerative Amplifiers via Intracavity Acousto-Optic Programmable Gain Control," in *Ultrafast Optics V* (Springer Berlin/Heidelberg, 2007), pp. 421-426.

11. T. Oksenhendler, D. Kaplan, P. Tournois, G. M. Greetham, and F. Estable, "Intracavity acousto-optic programmable gain control for ultra-wide-band regenerative amplifiers," Applied Physics B: Lasers and Optics 83, 491-494 (2006).

12. Clough, B., J. L. Liu, and X. C. Zhang, "*All air-plasma" terahertz spectroscopy*. Optics Letters., 2011 36(13): p. 2399-2401.

13. Dai, J., N. Karpowicz, and X. C. Zhang, *Coherent Polarization Control of Terahertz Waves Generated from Two-Color Laser-Induced Gas Plasma*. Physical Review Letters, 2009. 103(2): p. 023001.

The invention claimed is:

1. A method for agile remote generation of a broadband tunable short-pulse emission using a single laser beam, comprising generating copropagating ultrashort pulses with different wavelengths from a single laser beam and controlling independently each spectrum amplitude and phase and a relative delay between the pulses by spectral pulse shaping in the spectral domain, and spatially and temporally overlapping the pulses at a distance in a multiple-color filament, in a nonlinear optic medium.

2. The method of claim 1, wherein said controlling the delay between the pulses comprises applying a phase function or a superposition of phase functions in the spectral domain.

3. The method of claim 2, comprising applying a first order phase function in the spectral domain.

4. The method of claim 2, comprising applying a second order phase function in the spectral domain.

5. The method of claim 1, comprising modulating the laser spectrum into a first laser pulse and a second laser pulse having different central wavelengths, and combining the first pulse with the second pulse.

6. The method of claim 5, comprising modifying a wavelength of the first pulse by an optical parametric process, and combining a frequency modified part of the first pulse with the second pulse.

7. The method of claim 5, comprising frequency doubling the first pulse, and combining a frequency doubled part of the first pulse with the second pulse.

8. The method of claim 1, comprising modulating the original spectrum of the laser into a first laser pulse, a second laser pulse and a third pulse having different central wavelengths; adjusting a wavelength of at least one of the pulses by an optical parametric process, and combining a frequency adjusted part of the at least one pulse with the two other pulses into a filament.

9. The method of claim 8, wherein the first and the third pulses have an opposite equal wavelength difference with respect to the second pulse.

10. The method of claim 8, wherein the first and the third pulses have different wavelength differences with respect to the second pulse.

11. The method of claim 1, comprising modulating the laser spectrum into a first pulse, a second laser pulse and a third pulse having different central wavelengths; frequency doubling at least one of the pulses, and combining a frequency doubled part of the at least one pulse with the two other pulses into a filament.

12. The method of claim 11, wherein the first and the third pulses have an opposite equal wavelength difference with respect to the second pulse.

13. The method of claim 11, wherein the first and the third pulses have different wavelength differences with respect to the second pulse.

14. The method of claim 1, comprising modulating the laser spectrum into a first pulse, a second pulse and a third pulse having different central wavelengths; frequency doubling the second pulse, and combining a frequency doubled part of the second pulse with the first and third pulses into a filament.

15. The method of claim 14, wherein the first and the third pulses have an opposite equal wavelength difference with respect to the second pulse.

16. The method of claim 14, wherein the first and the third pulses have different wavelength differences with respect to the second pulse.

17. The method according to claim 1, comprising selecting a wavelength of a resulting emission by selecting a difference in wavelength between the pulses.

18. The method according to claim 1, comprising using one of a large spectrum laser and a multiple-band laser.

19. A method of generation of an optical source on a range of distance from a single laser beam, comprising modulating the single beam into colinear ultrashort pulses of different wavelengths, selecting at least two collinear pulses, controlling a relative delay between the pulses, and combining the selected pulses at a distance in a multiple-color filament, in a nonlinear optical medium.

20. A system for agile remote generation of a broadband tunable short-pulse emission in a non linear optical medium, comprising:

a mode-locked oscillator;

a pulse shaper in the spectral domain; and a non linear optical medium;

wherein said pulse shaper generates collinear ultrashort pulses of different wavelengths from a single broadband pulse from said oscillator and controls independently each spectrum amplitude and phase and a relative delay between the pulses, for spatially and temporally overlapping the pulses at a distance in a multiple-color filament in the nonlinear optical medium.

21. The system of claim 20, wherein said oscillator is one of: a large spectrum laser and a multiple-band laser.

22. The system of claim 20, wherein the pulse shaper is an AOPDF filter.

23. The system of claim 20, further comprising an amplifier.

* * * * *